US012776027B2

(12) United States Patent
Godden et al.

(10) Patent No.: US 12,776,027 B2
(45) Date of Patent: Oct. 27, 2026

(54) PREDICTIVE DATA ANALYSIS TECHNIQUES USING A HIERARCHICAL RISK PREDICTION MACHINE LEARNING FRAMEWORK

(71) Applicant: Optum Services (Ireland) Limited, Dublin (IE)

(72) Inventors: Paul J. Godden, London (GB); Melanie Majerus, Plymouth, MN (US); Ahmed Selim, Dublin (IE); Nancy Joan Mendelsohn, Mendota Heights, MN (US); Erin A. Satterwhite, West Lakeland, MN (US); Gregory J. Boss, Saginaw, MI (US)

(73) Assignee: Optum Services (Ireland) Limited, Dublin (IE)

( * ) Notice: Subject to any disclaimer, the term of this patent is extended or adjusted under 35 U.S.C. 154(b) by 1120 days.

(21) Appl. No.: 17/662,157

(22) Filed: May 5, 2022

(65) Prior Publication Data

US 2023/0360199 A1 Nov. 9, 2023

(51) Int. Cl.
*G06N 3/098* (2023.01)
*A61B 5/00* (2006.01)
(Continued)

(52) U.S. Cl.
CPC .......... *G06T 7/0012* (2013.01); *A61B 5/0077* (2013.01); *A61B 5/1079* (2013.01);
(Continued)

(58) Field of Classification Search
CPC ... G06T 7/0012; A61B 5/0077; A61B 5/1079; A61B 5/1128; A61B 5/7267; A61B 5/7275; G06N 3/096; G06N 3/098
See application file for complete search history.

(56) References Cited

U.S. PATENT DOCUMENTS

| | | | |
|---|---|---|---|
| 8,062,220 | B2 | 11/2011 | Kurtz et al. |
| 9,696,897 | B2 | 7/2017 | Garcia |

(Continued)

FOREIGN PATENT DOCUMENTS

| | | | |
|---|---|---|---|
| AU | 2019204376 B1 | 10/2020 | |
| WO | 2020/076416 A2 | 4/2020 | |

OTHER PUBLICATIONS

Lai et al "Capturing causality and bias in human action recognition" Pattern Recognition Letters, vol. 147, 2021, pp. 164-171, ISSN 0167-8655, https://doi.org/10.1016/j.patrec.2021.04.008 , https://www.sciencedirect.com/science/article/pii/S0167865521001380 (Year: 2021).*

(Continued)

*Primary Examiner* — Sanchita Roy
(74) *Attorney, Agent, or Firm* — Alston & Bird LLP

(57) ABSTRACT

Various embodiments of the present disclosure provide methods, apparatuses, systems, computing devices, computing entities, and/or the like for performing predictive data analysis operations using a hierarchical risk prediction machine learning framework that comprises an initially-deployed risk prediction machine learning model, a dynamically-deployed risk prediction machine learning model, and a risk aggregation machine learning model. In some embodiments, the dynamically-deployed risk prediction machine learning model is deployed when a dynamic deployment training entry count of one or more dynamic deployment training entries satisfies a dynamic deployment training entry count threshold.

20 Claims, 10 Drawing Sheets

(51) Int. Cl.
*A61B 5/107* (2006.01)
*A61B 5/11* (2006.01)
*G06N 3/096* (2023.01)
*G06T 7/00* (2017.01)
*G06T 17/00* (2006.01)

(52) U.S. Cl.
CPC .......... *A61B 5/1128* (2013.01); *A61B 5/7267* (2013.01); *A61B 5/7275* (2013.01); *G06N 3/096* (2023.01); *G06N 3/098* (2023.01); *G06T 17/00* (2013.01); *G06T 2207/20081* (2013.01); *G06T 2207/20084* (2013.01); *G06T 2207/30196* (2013.01)

(56) References Cited

U.S. PATENT DOCUMENTS

| | | | | |
|---|---|---|---|---|
| 9,996,739 | B2 | 6/2018 | Wu et al. | |
| 2019/0110754 | A1 | 4/2019 | Rao et al. | |
| 2020/0000373 | A1 | 1/2020 | Agrawal et al. | |
| 2020/0218974 | A1* | 7/2020 | Cheng | G06N 3/08 |
| 2020/0334524 | A1* | 10/2020 | Sprague | G06N 3/094 |
| 2021/0315486 | A1 | 10/2021 | Delp et al. | |
| 2022/0344049 | A1* | 10/2022 | Hall | G06N 3/098 |
| 2022/0351860 | A1* | 11/2022 | Aghaei | G06V 20/69 |
| 2022/0399132 | A1* | 12/2022 | Shah | G06N 3/082 |
| 2023/0025754 | A1* | 1/2023 | Hassanzadeh | G06N 20/00 |

OTHER PUBLICATIONS

"Computer Vision and Pattern Recognition—Authors and Titles For Recent Submissions," Jul. 2022, (10 pages), (online), [Retrieved from the Internet Jul. 14, 2022] <URL: https://arxiv.org/list/cs.CV/pastweek?skip=0&show=25>.

"Conditions + Treatments: Pediatric Neurological Examination Symptoms & Causes," Boston Children's Hospital, (6 pages), [Retrieved from the Internet Jul. 14, 2022] <URL: https://web.archive.org/web/20150926020713/https://www.childrenshospital.org/conditions-and-treatments/conditions/b/pediatric-neurological-examination/symptoms-and-causes>.

"Face2Gene is a Suite of Phenotyping Applications That Facilitate Comprehensive and Precise Genetic Evaluations," Face2Gene, (11 pages), (online), [Retrieved from the Internet Jul. 14, 2022] <URL: https://www.face2gene.com/>.

"Gait and Motion Analysis," Gillette Children's, (8 pages), (online), [Retrieved from the Internet Jul. 14, 2022] <URL: https://www.gillettechildrens.org/conditions-care/gait-and-motion-analysis>.

"Guide To The Comprehensive Pediatric H&P Write Up," (16 pages), (Year: 2022), Available Online: https://med.ucf.edu/media/2018/08/Guide-to-the-Comprehensive-Pediatric-H-and-P-Write-up.pdf.

"Live Better, Together!" Patients Like Me, (9 pages), (online), [Retrieved from the Internet Jul. 14, 2022] <URL: https://www.patientslikeme.com/>.

"Own Your Health. Advance Medicine," PicnicHealth, (10 pages), [Retrieved from the Internet Jul. 14, 2022] <URL: https://picnichealth.com/>.

"Rare Disease Search," FindZebra, (5 pages), (online), [Retrieved from the Internet Jul. 14, 2022] <URL: https://www.findzebra.com/>.

"Rare-X Patients' Data Powering Progress," Rare-X Rare Disease Database, (4 pages), (online), [Retrieved from the Internet Jul. 14, 2022] <URL: https://rare-x.org/>.

Babo, Cheryl. "Ryan's Stories," Cure Tay-Sachs Foundation, (3 pages), Aug. 2007, (article, online), [Retrieved from the Internet Jul. 14, 2022] <https://www.curetay-sachs.org/faRyans.jsp>.

Brunetti, Antonio et al. "Computer Vision and Deep Learning Techniques For Pedestrian Detection and Tracking: A Survey," Neurocomputing, vol. 300, Jan. 8, 2018, pp. 17-33, DOI: 10.1016/j.neucom.2018.01.092.

Chen, Chenyi. "Deep Learning For Self-Driving Car," Princeton Autonomous Vehicle Engineering (PAVE), (32 pages), [Retrieved from the Internet Jul. 14, 2022] <URL: https://www.princeton.edu/~alaink/Orf467F14/Deep%20Driving.pdf>.

Cohen, Jeremy. "Computer Vision and Deep Learning: From Image to Video Analysis," Heartbeat, Mar. 24, 2020, (18 pages), (article, online), [Retrieved from the Internet Jul. 14, 2022] <URL: https://heartbeat.comet.ml/computer-vision-from-image-to-video-analysis-d1339cf23961>.

Day, John. "Faculty Profiles In Excellence," Stanford Medicine Office of Faculty Development and Diversity, (8 pages), (online), [Retrieved from the Internet Jul. 14, 2022] <URL: https://med.stanford.edu/facultydiversity/faculty-community/faculty-profiles-in-excellence/column2/john_day_md_phd.html>.

Grigorescu, Sorin et al. "A Survey of Deep Learning Techniques for Autonomous Driving," arXiv PrePrint arXiv: 1910.07738v2 [cs.LG] Mar. 24, 2020, (28 pages).

Gupta, Abhishek et al. "Deep Learning For Object Detection and Scene Perception In Self-Driving Cars: Survey, Challenges, and Open Issues," Array, vol. 10, No. 100057, Jan. 26, 2021, pp. 1-20, DOI: 10.1016/j.array.2021.100057.

Huang, Gao et al. "Densely Connected Convolutional Networks," arXiv PrePrint arXiv: 1608.06993v5 [cs.CV] Jan. 28, 2018, pp. 1-9.

Huval, Brody et al. "An Empirical Evaluation of Deep Learning on Highway Driving," arXiv Preprint arXiv:1504.01716v3 [cs.RO] Apr. 17, 2015, pp. 1-7, Available Online: https://arxiv.org/pdf/1504.01716.pdf.

Jiao, Licheng et al. "A Survey of Deep Learning-Based Object Detection," arXiv PrePrint arXiv: 1907.09408v2 [cs.CV] Oct. 10, 219, pp. 1-30.

Kidzinski, Lukasz et al. "Deep Neural Networks Enable Quantitative Movement Analysis Using Single-Camera Videos," Nature Communications, vol. 11, No. 1, pp. 1-10, Aug. 13, 2020, DOI: 10.1038/s41467-020-17807-z.

Kotagal, Suresh et al. "Detailed Neurologic Assessment of Infants and Children," UpToDate, Jun. 8, 2022, (13 pages), [Retrieved from the Internet Jul. 14, 2022] <URL: https://www.medilib.ir/uptodate/show/15360>.

Nieto-Hidalgo, Mario et al. "Gait Analysis Using Computer Vision Based On Cloud Platform and Mobile Device," Hindawi Mobile Information Systems, vol. 2018, Article ID 7381264, pp. 1-10, DOI: 10.1155/2018/7381264.

Rosebrock, Adrian. "Measuring Size of Objects in an Image With OpenCV," PYImageSearch, Jul. 8, 2021, (161 pages), (article, online), [Retrieved from the Internet Jul. 14, 2022] <URL: https://pyimagesearch.com/2016/03/28/measuring-size-of-objects-in-an-image-with-opencv/>.

Sadek, Esraa T. et al. "Computer Vision Techniques For Autism Symptoms Detection and Recognition: A Survey," International Journal of Intelligent Computing and Information Sciences, vol. 20, No. 2, pp. 89-111, DOI: 10.21608/IJICIS.2020 46360.1034.

Sapiro, Guillermo et al. "Computer Vision Applications To Computational Behavioral Phenotying: An Autism Spectrum Disorder Case Study," Current Opinion in Biomedical Engineering, vol. 9, pp. 14-20, Mar. 1, 2019.

Venables, Michelle. "An Overview of Computer Vision," Towards Data Science, Sep. 10, 2019, (7 pages), (article, online), [Retrieved from the Internet Jul. 14, 2022] <https://towardsdatascience.com/an-overview-of-computer-vision-1175c2ab1b66>.

Wu, Ann Chen et al. "Ending The Diagnostic Odyssey: Is Whole Genome Sequencing The Answer?" JAMA Pediatrics. vol. 174, No. 9, pp. 821-822, Sep. 1, 2020, DOI: 10.1001/jamapediatrics.2020.1522.

Zadeh, Mohammad Zaki et al. "Automated System To Measure Tandem Gait To Assess Executive Functions in Children," In The 14th Pervasive Technologies Related to Assistive Environments Conference, Jun. 29, 2021, pp. 167-170, DOI: 10.1145.3453892.3453999.

* cited by examiner

FIG. 7
700
HYGIEIA
Please enter your child's age
Please enter your child's gender.
How many siblings does your child have?
Does your child have any pre-existing medical conditions?
Do you or your partner have any known inherited conditions?
Please enter any concerns, issues worries or other considerations relating to your child's health or development.

FIG. 8
Bilateral arm flexion detected
Extended gait detected

800

PREDICTIVE DATA ANALYSIS TECHNIQUES USING A HIERARCHICAL RISK PREDICTION MACHINE LEARNING FRAMEWORK

BACKGROUND

Various embodiments of the present invention address technical challenges related to performing predictive analysis and disclose innovative techniques for efficiently and effectively performing predictive data analysis operations using a hierarchical risk prediction machine learning framework.

BRIEF SUMMARY

In general, various embodiments of the present disclosure provide methods, apparatuses, systems, computing devices, computing entities, and/or the like for performing predictive data analysis operations using a hierarchical risk prediction machine learning framework. Certain embodiments of the present invention utilize systems, methods, and computer program products that perform predictive data analysis using initially-deployed risk prediction machine learning models, dynamically-deployed risk prediction machine learning models, and risk aggregation machine learning models.

In accordance with one aspect, a computer-implemented method for generating a predicted risk score for an input feature data object is provided. In one embodiment, the method comprises: generating, by one or more processors and based at least in part on the input feature data object, an input deidentified three-dimensional model; generating, by the one or more processors, based at least in part on the input deidentified three-dimensional model, and using a dynamically-deployed risk prediction machine learning model, the predicted risk score, wherein: the dynamically-deployed risk prediction machine learning model is deployed when a dynamic deployment training entry count of one or more dynamic deployment training entries satisfies a dynamic deployment training entry count threshold, the dynamically-deployed risk prediction machine learning model is trained using the one or more dynamic deployment training entries, each dynamic deployment training entry comprises a corresponding training entry deidentified three-dimensional model that is associated with a corresponding training entry feature data object and a corresponding dynamic deployment ground-truth indicator, each corresponding dynamic deployment ground-truth indicator of a corresponding dynamic deployment training entry is determined based at least in part on a corresponding recommendation validation indicator for a corresponding predicted recommendation that is generated based at least in part on an initial risk score, and each initial risk score is generated by an initially-deployed risk prediction machine learning model based at least in part on an identifiable feature data object for the corresponding dynamic deployment training entry; and performing, by the one or more processors, one or more prediction-based actions based at least in part on the predicted risk score.

In accordance with another aspect, an apparatus for generating a predicted risk score for an input feature data object is provided. The apparatus may comprise at least one processor and at least one memory including computer program code is provided. In one embodiment, the at least one memory and the computer program code may be configured to, with the processor, cause the apparatus to: generate, based at least in part on the input feature data object, an input deidentified three-dimensional model; generate, based at least in part on the input deidentified three-dimensional model, and using a dynamically-deployed risk prediction machine learning model, the predicted risk score, wherein: the dynamically-deployed risk prediction machine learning model is deployed when a dynamic deployment training entry count of one or more dynamic deployment training entries satisfies a dynamic deployment training entry count threshold, the dynamically-deployed risk prediction machine learning model is trained using the one or more dynamic deployment training entries, each dynamic deployment training entry comprises a corresponding training entry deidentified three-dimensional model that is associated with a corresponding training entry feature data object and a corresponding dynamic deployment ground-truth indicator, each corresponding dynamic deployment ground-truth indicator of a corresponding dynamic deployment training entry is determined based at least in part on a corresponding recommendation validation indicator for a corresponding predicted recommendation that is generated based at least in part on an initial risk score, and each initial risk score is generated by an initially-deployed risk prediction machine learning model based at least in part on an identifiable feature data object for the corresponding dynamic deployment training entry; and perform one or more prediction-based actions based at least in part on the predicted risk score.

In accordance with yet another aspect, a computer program product for generating a predicted risk score for an input feature data object is provided. The computer program product may comprise at least one computer-readable storage medium having computer-readable program code portions stored therein, the computer-readable program code portions comprising executable portions configured to: generate, based at least in part on the input feature data object, an input deidentified three-dimensional model; generate, based at least in part on the input deidentified three-dimensional model, and using a dynamically-deployed risk prediction machine learning model, the predicted risk score, wherein: the dynamically-deployed risk prediction machine learning model is deployed when a dynamic deployment training entry count of one or more dynamic deployment training entries satisfies a dynamic deployment training entry count threshold, the dynamically-deployed risk prediction machine learning model is trained using the one or more dynamic deployment training entries, each dynamic deployment training entry comprises a corresponding training entry deidentified three-dimensional model that is associated with a corresponding training entry feature data object and a corresponding dynamic deployment ground-truth indicator, each corresponding dynamic deployment ground-truth indicator of a corresponding dynamic deployment training entry is determined based at least in part on a corresponding recommendation validation indicator for a corresponding predicted recommendation that is generated based at least in part on an initial risk score, and each initial risk score is generated by an initially-deployed risk prediction machine learning model based at least in part on an identifiable feature data object for the corresponding dynamic deployment training entry; and perform one or more prediction-based actions based at least in part on the predicted risk score.

BRIEF DESCRIPTION OF THE DRAWINGS

Figure 1:
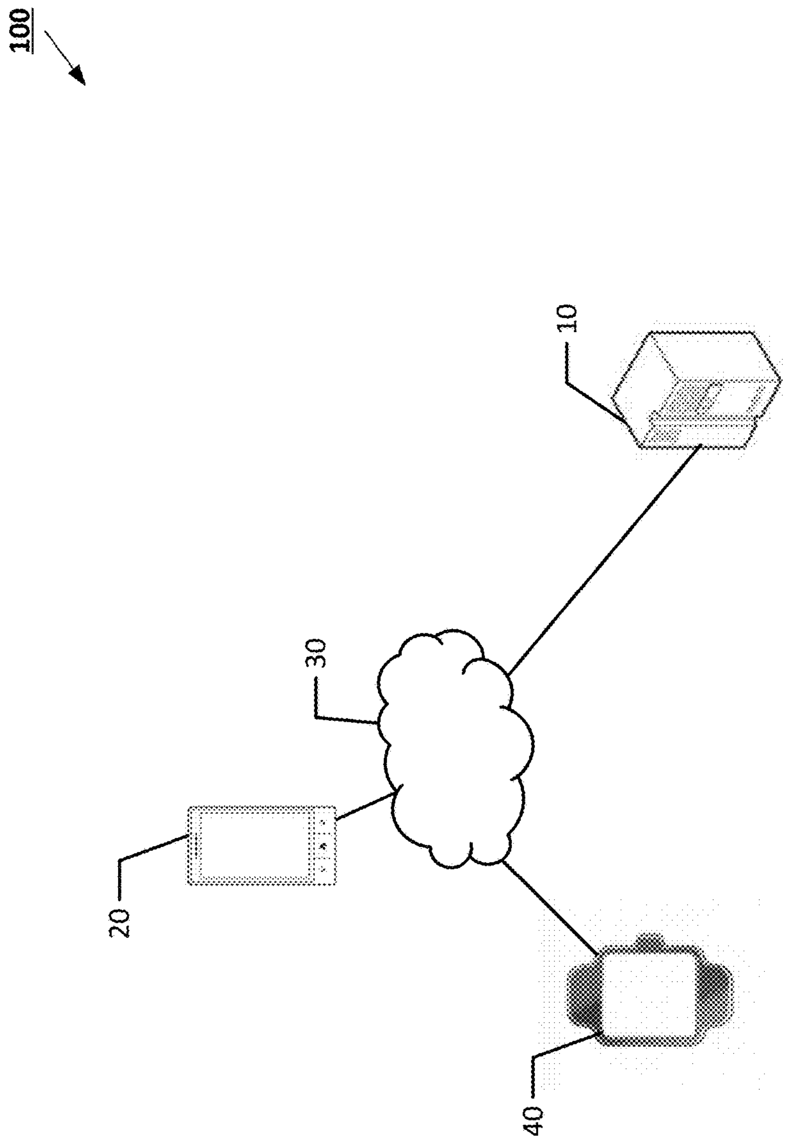
Figure 2:
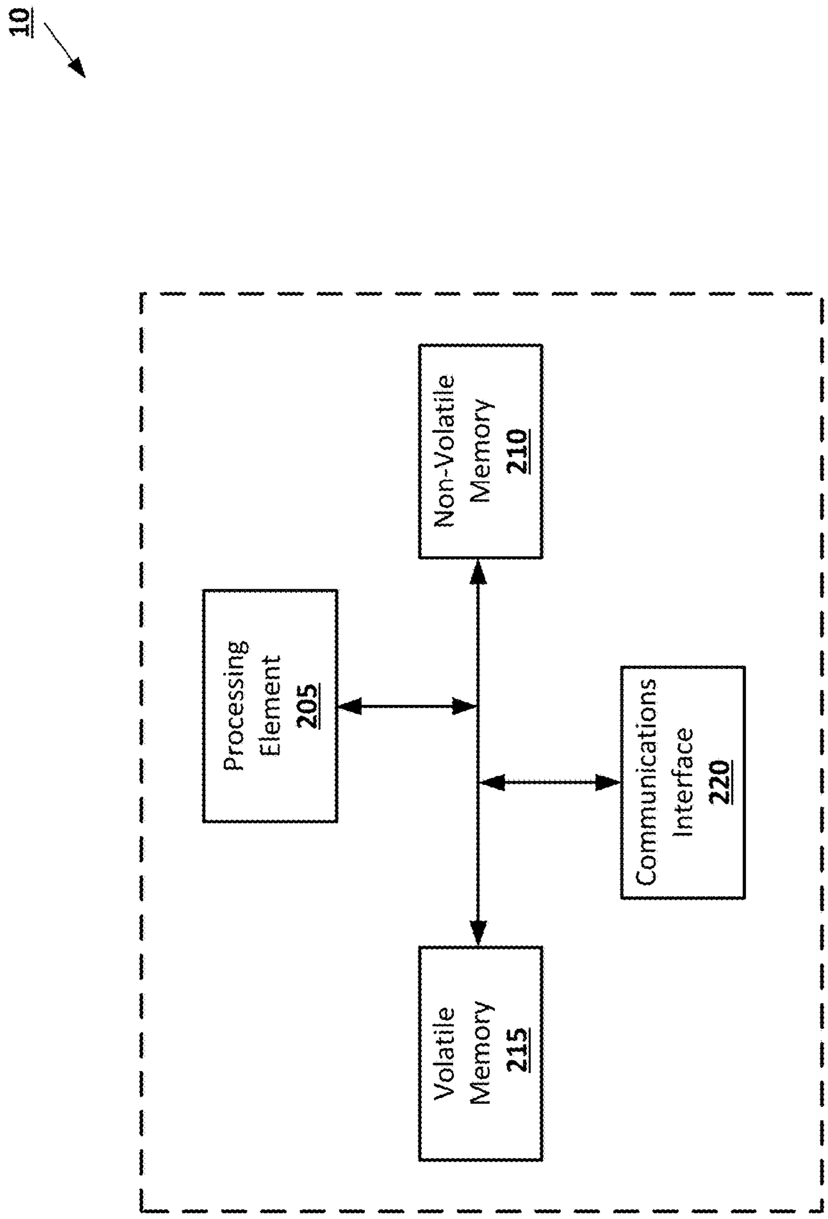
Figure 3:
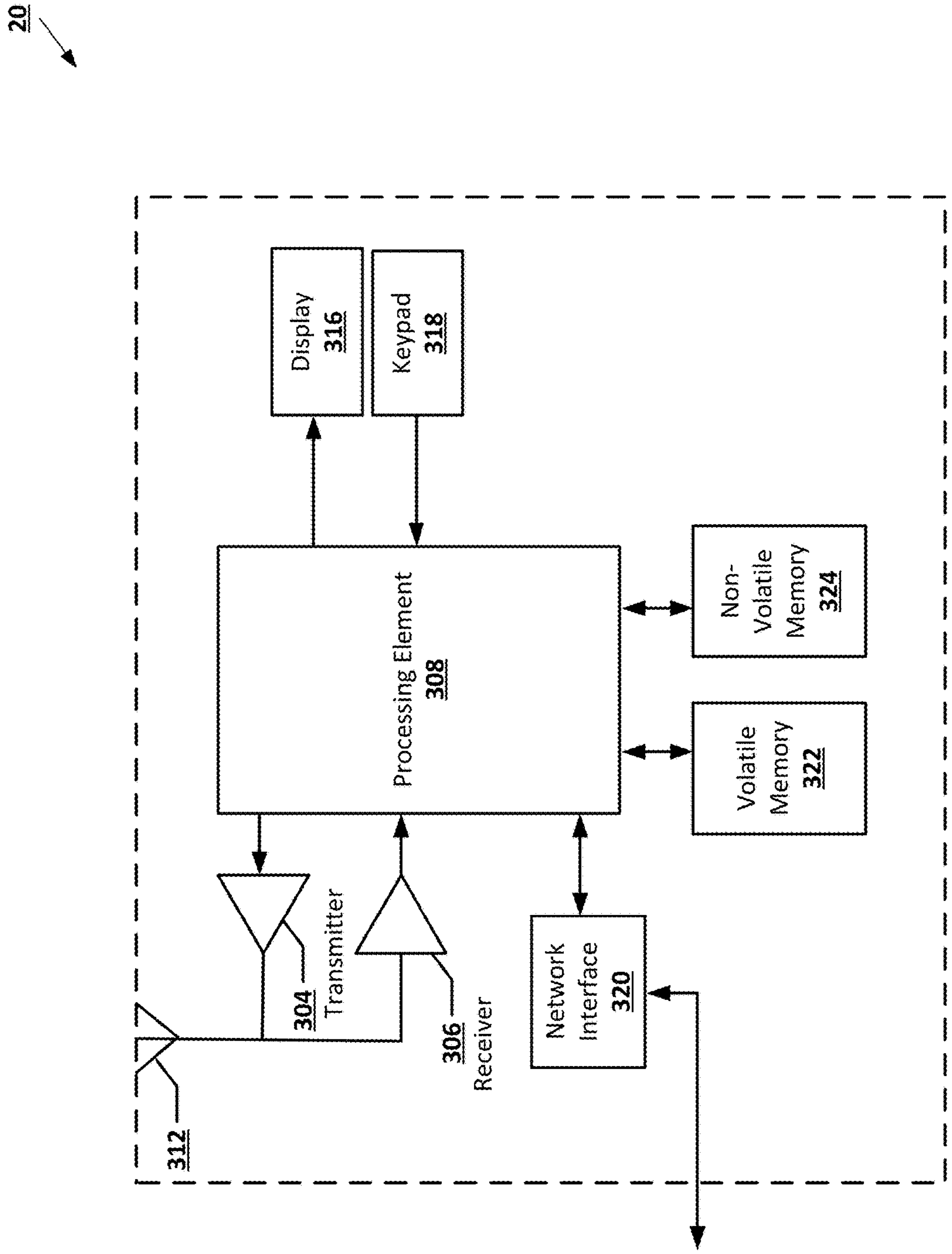
Figure 4:
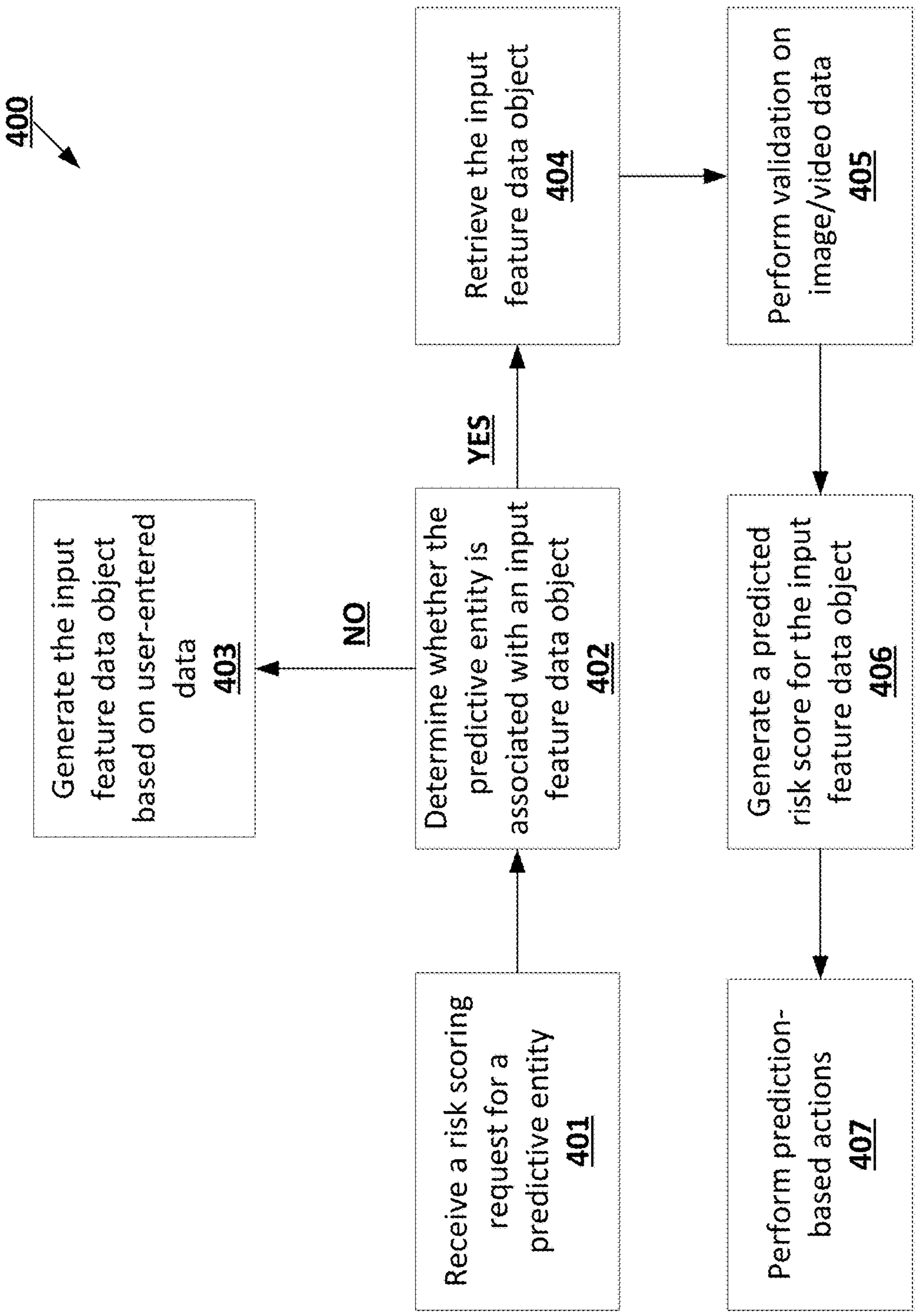
Figure 5A:
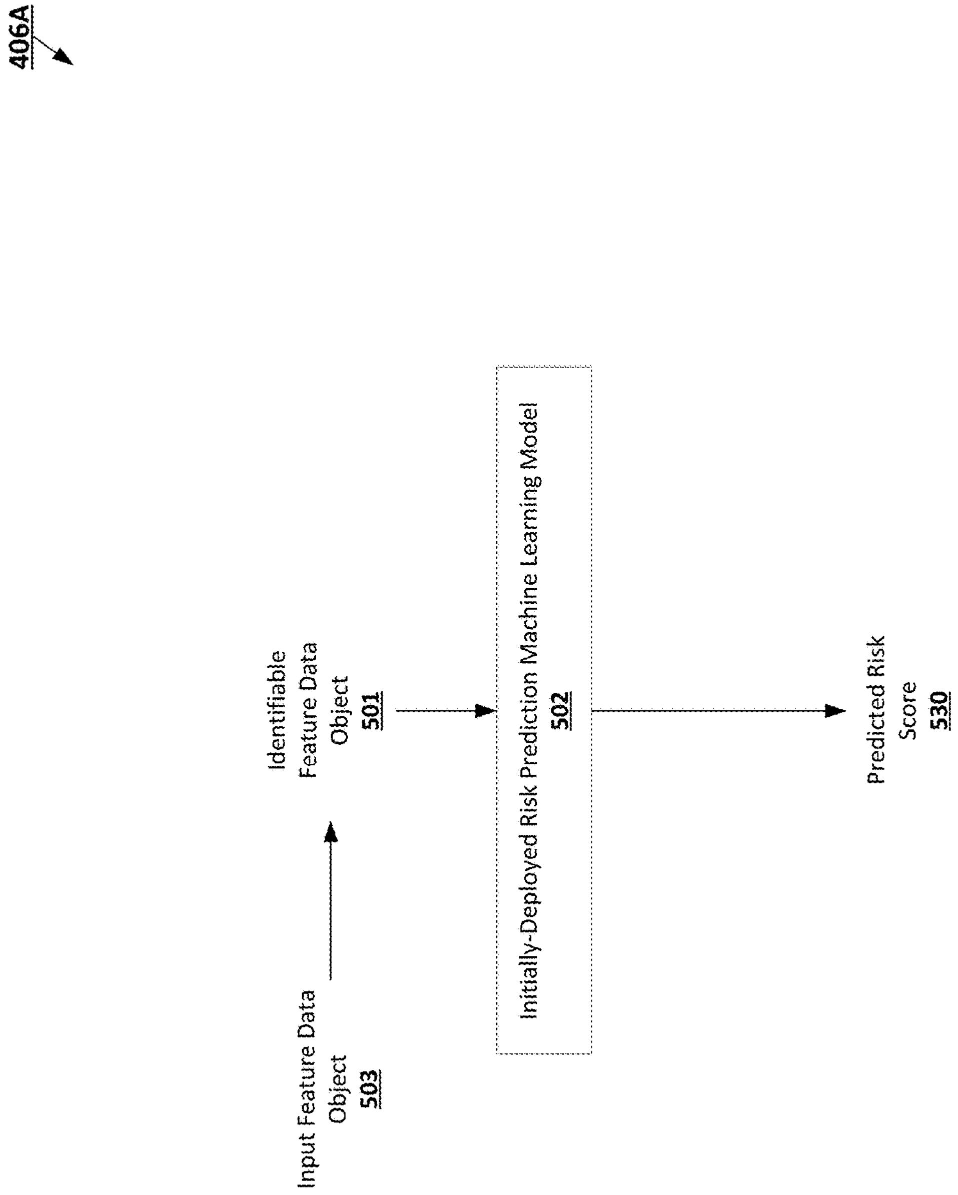
Figure 5B:
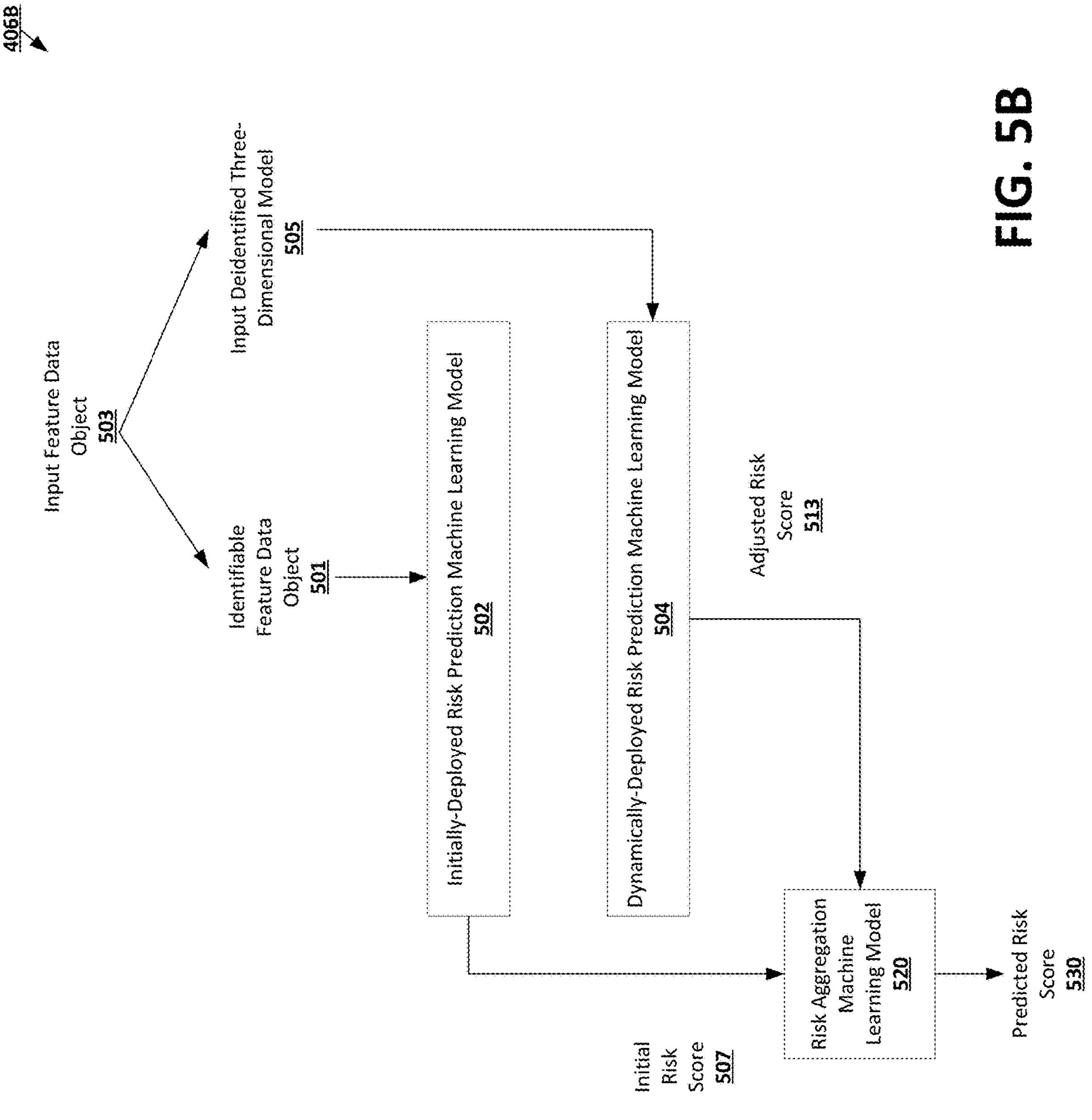
Figure 6:
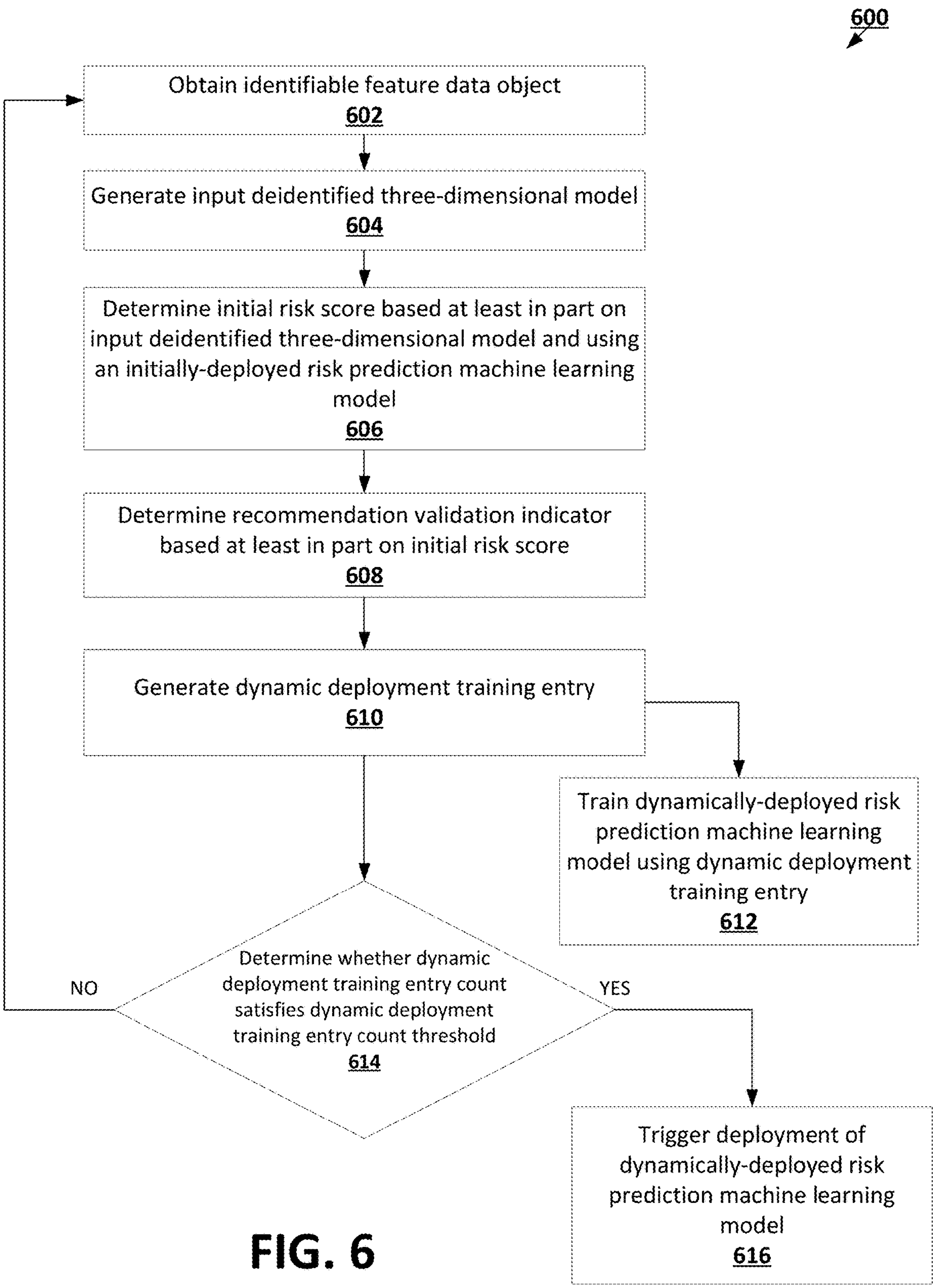
Figure 7:
Figure 8:
Figure 9A:
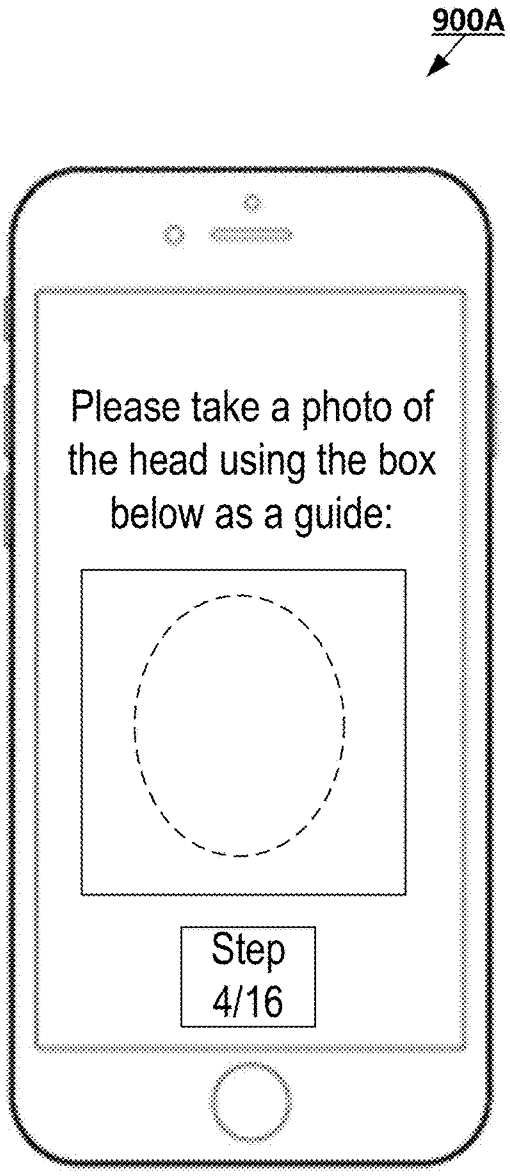
Figure 9B:
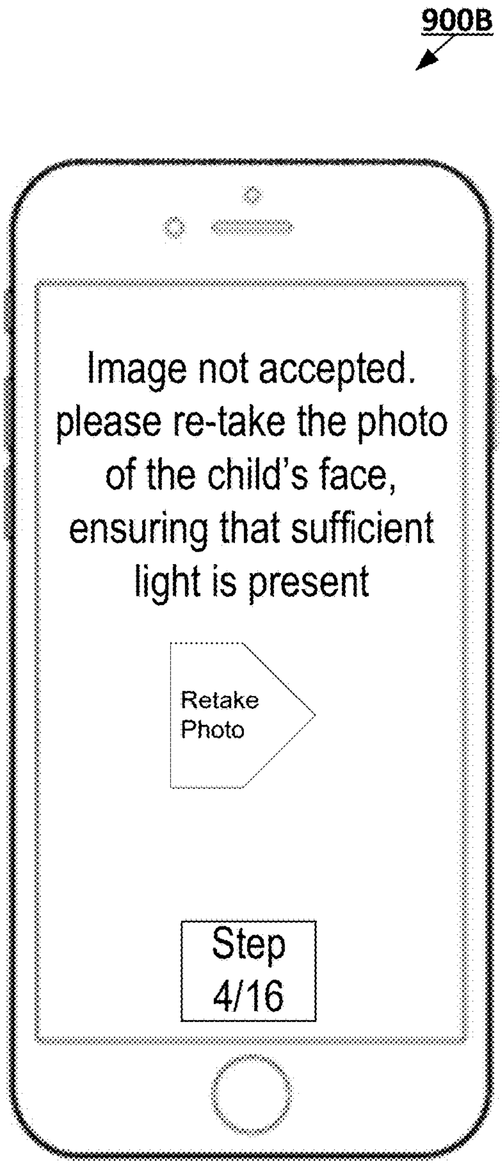

Having thus described the invention in general terms, reference will now be made to the accompanying drawings, which are not necessarily drawn to scale, and wherein:

FIG. 1 is an exemplary overview of a system architecture that can be used to practice various embodiments of the present disclosure;

FIG. 2 is an example schematic of a risk prediction computing entity in accordance with certain embodiments of the present disclosure;

FIG. 3 is an example schematic of a user computing entity in accordance with certain embodiments of the present disclosure;

FIG. 4 is an example schematic of a risk prediction system in accordance with certain embodiments of the present disclosure;

FIG. 5A is an example schematic diagram illustrating an operational example in accordance with some embodiments of the present disclosure;

FIG. 5B is another example schematic diagram illustrating an operational example in accordance with some embodiments of the present disclosure;

FIG. 6 is a flowchart diagram illustrating an example process in accordance with certain embodiments of the present disclosure;

FIG. 7 is an example view of a user interface, in accordance with certain embodiments of the present disclosure;

FIG. 8 is an example schematic diagram illustrating an operational example in accordance with some embodiments of the present disclosure;

FIG. 9A is an example view of a user interface, in accordance with certain embodiments of the present disclosure; and FIG. 9B is another example view of a user interface, in accordance with certain embodiments of the present disclosure.

DETAILED DESCRIPTION

Various embodiments of the present disclosure now will be described more fully hereinafter with reference to the accompanying drawings, in which some, but not all embodiments are shown. Indeed, various configurations as discussed herein may be embodied in many different forms and should not be construed as limited to the embodiments set forth herein; rather, these embodiments are provided so that this disclosure will satisfy applicable legal requirements. The term "or" (also designated as "I") is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview and Technical Advantages

Various embodiments of the present invention describe techniques for increasing efficiency of machine learning frameworks while maintaining the outputs of the machine learning frameworks within a desired threshold accuracy/reliability range. For example, in some embodiments, a hierarchical machine learning framework includes an initially-deployed component and a dynamically-deployed component, where the initially-deployed component is trained using training data that is available before deployment of the hierarchical machine learning framework but is expected to be less accurate, while the dynamically-deployed component is trained using training data that is available after deployment of the hierarchical machine learning framework but is expected to be more accurate. This approach ensures that, before the training data for the dynamically-deployed component is available, the hierarchical machine learning framework only comprises the initially-deployed component and thus avoids the need for performing computational instructions associated with executing operations of the dynamically-deployed component of the hierarchical machine learning framework. In this way, by disclosing a hierarchical machine learning framework including an initially-deployed component and a dynamically-deployed component, various embodiments of the present invention introduce techniques for increasing efficiency of machine learning frameworks while maintaining the outputs of the machine learning frameworks within a desired threshold accuracy/reliability range.

Various embodiments of the present invention improve data security of implementing machine learning frameworks using a client-server architecture, where the input features of a machine learning framework are provided by a client device to a predictive data analysis server system. For example, in some embodiments, at least part of the input data provided by the client device (e.g., image/video data associated with an identifiable feature data object) are removed after performing predictive inferences and thus not permanently maintained. In some embodiments, an input feature data object is associated with an identifiable feature data object that is removed from a storage subsystem associated with a predictive data analysis system after generating a predictive output (e.g., an initial risk and/or a predicted risk score) based at least in part on the input feature data object. In some embodiments, an input feature data object is associated with a deidentified three-dimensional model that is permanently stored and/or not removed from a storage subsystem associated with a predictive data analysis system after generating a predictive output (e.g., an initial risk and/or a predicted risk score) based at least in part on the input feature data object. In some embodiments, the deidentified three-dimensional model is used as input data for a dynamically-deployed component of a machine learning framework, while the identifiable feature data object is used as input data for an initially-deployed component of the machine learning framework. In this way, if the predictive data analysis system is compromised, only permanently-stored data (e.g., de-identified data) are comprised, while identifiable data are not compromised. In this way, by ensuring that at least part of the input data provided by the client device (e.g., image/video data associated with an identifiable feature data object) are removed after performing predictive inferences and thus not permanently maintained, various embodiments of the present invention improve data security of implementing machine learning frameworks using a client-server architecture, where the input features of a machine learning framework are provided by a client device to a predictive data analysis server system.

Various embodiments of the present invention introduce techniques for improving operational reliability and computational efficiency of predictive data analysis solutions by using a hierarchical risk prediction machine learning framework. As further described herein, a hierarchical risk prediction machine learning framework may generate predictive outputs using an initially-deployed risk prediction machine learning model and use the outputs of the initially-deployed risk prediction machine learning model to generate training data for a dynamically-deployed risk prediction machine learning model. Additionally, the hierarchical risk prediction machine learning framework may include a risk aggregation machine learning model that is configured to generate a final predictive output based at least in part on intermediary outputs generated by other machine learning models. In some embodiments, the outputs generated by the initially-deployed risk prediction machine learning model may be anonymized and deidentified to provide comprehensive training data that excludes personally identifiable information (PII). Additionally, using the noted hierarchical framework, deployment of the dynamically-deployed risk prediction machine learning model may be deferred until a target performance threshold is reached. Accordingly, by using a hierarchical risk prediction machine learning framework, various embodiments of the present invention optimize and improve the process of training risk prediction machine learning models while facilitating generation of useful predictive outputs during the training process. Thus, the solutions described herein improve operational reliability and computational efficiency of risk prediction data analysis solutions.

Various embodiments of the present invention disclose techniques for more efficiently and reliably performing predictive data analysis. For example, various embodiments of the present invention disclose techniques for performing predictive data analysis operations utilizing a hierarchical risk prediction machine learning framework. For example, according to some embodiments of the present invention, predictive data analysis using a hierarchical risk prediction machine learning framework can be performed by: (i) generating an initial risk score associated with an input feature data object using an initially-deployed risk prediction machine learning model of the hierarchical risk prediction machine learning framework, (ii) generating an adjusted risk score associated with an input feature data object using a dynamically-deployed risk prediction machine learning model of the hierarchical risk prediction machine learning framework, (iii) generating a predicted risk score using a risk aggregation machine learning model of the hierarchical risk prediction machine learning framework based at least in part on the initial risk score and the adjusted risk score, and (iv) performing one or more prediction-based actions based at least in part on the predicted risk score.

In some embodiments, the dynamically-deployed risk prediction machine learning model of the hierarchical risk prediction machine learning framework utilizes training data and prediction operations that may, in at least some embodiments, reduce or eliminate the need for deferring the deployment of a predictive data analysis solution due to computationally expensive and extensive training operations. By deploying certain components of the hierarchical risk prediction machine learning framework while performing training operations, various embodiments of the present invention improve the computational efficiency of performing predictive data analysis. Via the noted advantages, various embodiments of the present invention make substantial technical contributions to the fields of predictive data analysis in particular and healthcare-related predictive data analysis in general.

An exemplary application of various embodiments of the proposed invention relates to predicting rare disease (RD) with respect to individuals (e.g., children) based at least in part on image/video sensor data, patient medical history, and the like. A great challenge for RD patients is a long journey to diagnosis, sometime referred to as a diagnostic odyssey (DO), which may be costly, time consuming, and difficult for patients and family members alike to navigate. For example, there are approximately 7,000 different known RDs (e.g., hemophilia, sickle cell, and muscular dystrophy) and identifying the cause of a patient's affliction may prove extremely challenging.

An exemplary application of various embodiments of the proposed invention relates to a "virtual triage" application (app), that utilizes deep learning and computer vision techniques to provide a mechanism to reduce the length of a DO, and thus ameliorate the burden faced by patients and their families. The techniques discloses herein provide a framework for concerned parents to be guided by an app, enabling them to "raise their hand" and infer if their child may have a RD, before being connected to a specialist, or a Centre of Excellence (CoE). Consequently, the invention may reduce the length of the DO in the case of a candidate RD patient and provides techniques to help address the challenges described above.

Another exemplary application of various embodiments of the proposed invention relates to a diagnostic support tool (e.g., a physician may ask a parent to download an app and walk through a protocol). In some embodiments, aspects of the present invention enable a user to obtain a diagnosis, identify specialists, obtain medical instructions, plan a consultation, understand a prognosis, identify risks for other family members, and provide a community for patients with similar diagnoses.

II. Definitions of Certain Terms

The term "body" may refer to a person's physical form, and the term may specifically be utilized to refer to a portion of a person's body, including at least a portion of one or more internal and/or external organs of a user. In general, the terms user, patient, wearer, individual, person and/or similar words are used herein interchangeably.

The term "predictive entity" may refer to a data object that describes an entity with respect to which one or more predictive tasks/operations are performed. In some embodiments, a predictive entity may refer to a data object that describes an individual (e.g., child, patient, member, or the like). The individual may be associated with a health insurance insurer and may be considered a member of a program associated with the health insurance insurer. An example predictive entity may correspond with an identifier (e.g., patient name, member ID, and/or the like).

The term "initially-deployed risk prediction machine learning model" may refer to a data object that describes operations, parameters, and/or hyperparameters of a machine learning model that is configured to process an identifiable feature data object (e.g., comprising image and/or video sensor data) of a predictive entity in order to generate a predictive output for the predictive output. An example output from the initially-deployed risk determination machine learning model may be or comprise an initial risk score. In some embodiments, the initially-deployed risk determination machine learning model may be used prior to the deployment of a dynamically-deployed risk prediction machine learning model (e.g., in an instance in which a dynamic deployment training entry count of one or more dynamic deployment training entries fails to satisfy a dynamic deployment training entry count threshold). In some embodiments, the output of an initially-deployed risk prediction machine learning model may be used to generate training data (e.g., training entry deidentified three-dimensional models) for training a dynamically-deployed risk prediction machine learning model. An example of an initially-deployed risk determination machine learning model is a trained supervised machine learning model (e.g., a trained supervised regression model, a convolutional neural network model, and/or the like) and/or an image-based classification machine learning component.

The term "identifiable feature data object" may refer to a data object that describes identifiable features associated with an individual including, but not limited to, a three-dimensional movement profile, one or more three-dimensional body-related characteristics, patient information/data (e.g., historical claim data), contextual features associated with an individual/related entities (e.g., from medical data and/or social media data), based at least in part on an operational context of a machine learning model (e.g., physical environment of the image/video data associated with the identifiable feature data object), and/or the like. In some embodiments, an identifiable feature data object may be an example input for an initially-deployed risk prediction machine learning model.

The term "input feature data object" may refer to a data object that describes features associated with a predictive entity such as an individual, and with respect to which one or more predictive tasks/operations are performed. In some embodiments, an input feature data object may refer to a data object that describes features of a patient, member, or the like. In various embodiments, an input feature data object may be used to generate or may be associated with an identifiable feature data object and/or an input deidentified three-dimensional model, which in turn may be used to determine a predicted risk score. In some embodiments, an input feature data object is associated with an identifiable feature data object that is removed from a storage subsystem associated with a predictive data analysis system after generating a predictive output (e.g., an initial risk and/or a predicted risk score) based at least in part on the input feature data object. In some embodiments, an input feature data object is associated with a deidentified three-dimensional model that is permanently stored and/or not removed from a storage subsystem associated with a predictive data analysis system after generating a predictive output (e.g., an initial risk and/or a predicted risk score) based at least in part on the input feature data object.

The term "initial risk score" may refer to a data object that describes a predictive output of one or more computer-implemented processes, wherein the predictive output describes an inferred measure of risk with respect to an identifiable feature data object. In some embodiments, the predicted risk score may be related to whether an individual is likely to have a rare disease and/or should be referred for a rare disease screening/investigation (e.g., Deoxyribonucleic Acid (DNA) sequencing/testing, clinician review, and/or the like). The example initial risk score may be an output of an initially-deployed risk prediction machine learning model (e.g., the initially-deployed risk prediction machine learning model may be used in an instance in which a dynamic deployment training entry count of one or more dynamic deployment training entries fails to satisfy a dynamic deployment training entry count threshold). In some embodiments, the initial risk score may be an intermediary output of a hierarchical risk prediction machine learning framework that comprises a plurality of machine learning models.

The term "dynamically-deployed risk prediction machine learning model" may refer to a data object that describes operations, parameters, and/or hyperparameters of a machine learning model that is configured to process an input feature data object in order to generate an input deidentified three-dimensional model that can be used to generate a predicted risk score. In some embodiments, the dynamically-deployed risk determination machine learning model may be trained using one or more dynamic deployment training entries where each dynamic deployment training entry comprises a corresponding training entry deidentified three-dimensional model that is associated with a corresponding training entry feature data object and a corresponding dynamic deployment ground-truth indicator. In some embodiments, the dynamically-deployed risk prediction machine learning model is deployed in response to determining that a dynamic deployment training entry count of one or more dynamic deployment training entries satisfies a dynamic deployment training entry count threshold. In some embodiments, each corresponding dynamic deployment ground-truth indicator of a corresponding dynamic deployment training entry is determined based at least in part on a corresponding recommendation validation indicator for a corresponding predicted recommendation that may be generated based at least in part on/associated with an initial risk score. An example of a dynamically-deployed risk determination machine learning model is a trained supervised machine learning model (e.g., a trained supervised regression model, a convolutional neural network model, and/or the like) and/or an image-based classification machine learning component. In some embodiments, an example input to the dynamically-deployed risk prediction machine learning model may be or comprise an input feature data object. An example output from the dynamically-deployed risk determination machine learning model may be or comprise a predicted risk score. The operations of the dynamically-deployed risk determination machine learning model may lead to performing one or more prediction-based actions or tasks.

The term "adjusted risk score" may refer to a data object that describes a predictive output of one or more computer-implemented processes, wherein the predictive output describes an inferred measure of risk with respect to an input deidentified three-dimensional model. The adjusted risk score may be used to generate a predicted risk score. In some embodiments, the predicted risk score may be related to whether an individual is likely to have a rare disease and/or should be referred for a rare disease screening/investigation. The example initial risk score may be an output of a dynamically-deployed risk prediction machine learning model where the dynamically-deployed risk prediction machine learning model is used in an instance in which a dynamic deployment training entry count of one or more dynamic deployment training entries satisfies a dynamic deployment training entry count threshold. In some embodiments, the adjusted risk score may be an intermediary output of a hierarchical risk prediction machine learning framework that comprises a plurality of machine learning models.

The term "risk aggregation machine learning model" may refer to a data object that describes operations, parameters, and/or hyperparameters of a machine learning model that is configured to process an initial risk score and an adjusted risk score in order to generate a predicted risk score. In some embodiments, the initial risk score is an output of an initially-deployed risk prediction machine learning model, and the adjusted risk score is an output of a dynamically-deployed risk prediction machine learning model. In some embodiments, the risk aggregation machine learning model is a supervised machine learning model or an unsupervised machine learning model (e.g., a clustering model). In some embodiments, inputs to the risk aggregation machine learning model comprise a vector describing the initial risk score and the adjusted risk score, while outputs of the risk aggregation machine learning model comprise a vector describing the predicted risk score.

The term "predicted risk score" may refer to a data object that describes a predictive output of one or more computer-implemented processes, wherein the predictive output describes an inferred measure of risk with respect to an input feature data object and/or input deidentified three-dimensional model. In some embodiments, the predicted risk score may be related to whether or an individual that is associated with the input feature data object is likely to have a rare disease and/or should be referred for a rare disease screening/investigation (e.g., DNA sequencing/testing, clinician review, and/or the like). By way of example, the predicted risk score may be a value where an above-threshold value indicates that a particular individual is likely to have a rare disease and/or should be referred for a rare disease screening/investigation. The example predicted risk score may be generated using an initially-deployed risk prediction machine learning model and/or a dynamically-deployed risk prediction machine learning model (in some embodiments, based at least in part on an initial risk score and/or an adjusted risk score) and may be used to perform one or more prediction-based actions with respect to the input feature data object. In some embodiments, the predicted risk score may be a final output of a hierarchical risk prediction machine learning framework that comprises a plurality of machine learning models.

The term "dynamic deployment training entry count threshold" may refer a parameter, condition, value, or the like that defines count of dynamic deployment training entries that must be satisfied in order to trigger deployment of a dynamically-deployed risk determination machine learning model. In some embodiments, an example dynamic deployment training entry may be or comprise a data object that describes or is otherwise associated with a training entry deidentified three-dimensional model that can be used to train a dynamically-deployed risk determination machine learning model.

The term "input deidentified three-dimensional model" may refer to a data object that describes a predictive output of one or more computer-implemented processes, wherein the predictive output describes a deidentified three-dimensional movement profile and/or one or more three-dimensional body related characteristics. In some embodiments, an input deidentified three-dimensional model may be associated with a dynamic deployment training entry. In some embodiments, an example input deidentified three-dimensional model may be generated based at least in part on an input feature data object describing identifiable features of an individual (e.g., patient, member, or the like).

The term "three-dimensional movement profile" may refer to a data object that describes a predictive output of one or more computer-implemented processes, wherein the predictive output describes at least one movement feature set describing a three-dimensional representation of an individual's gait. In some embodiments, a three-dimensional movement profile may be generated based at least in part on image/video sensor data associated with an individual.

The term "three-dimensional body-related characteristics" may refer to a data object that describes at least one feature set describing a three-dimensional representation of an individual's physical characteristics. In various embodiments, three-dimensional body-related characteristics may include holistic characteristics, head and face characteristics, posture, muscle tone, and arm and hand characteristics. In some embodiments, three-dimensional body-related characteristics may be determined based at least in part on image/video sensor data associated with an individual.

The term "deidentified three-dimensional model" may refer to a data object that describes an anonymized/deidentified three-dimensional model/representation (e.g., comprising a deidentified three-dimensional movement profile and/or one or more three-dimensional body-related characteristics). For example, a dynamic deployment training entry may comprise a training entry deidentified three-dimensional model that is in turn associated with a corresponding training entry feature data object and a corresponding dynamic deployment ground-truth indicator. In some embodiments, a training entry deidentified three-dimensional model may be used as input to train a dynamically-deployed risk determination machine learning model.

The term "dynamic deployment ground-truth indicator" may refer to a data object that describes a validated outcome of a rare disease screening or investigation. In some embodiments, the dynamic deployment ground-truth indicator may be or comprise a determined recommendation validation indicator with respect to a training entry feature data object. For example, a dynamic deployment ground-truth indicator may be associated with a training entry feature data object describing features/attributes of a deidentified individual that is diagnosed as having a rare disease (e.g., as a result of a recommended rare disease screening/investigation).

The term "recommendation validation indicator" may refer to a data object that describes a determination relating to a degree of correspondence between a risk score (e.g., initial risk score or predicted risk score) associated with a predicted recommendation and a validated outcome of a rare disease screening/investigation. By way of example, if a predicted risk score/initial risk score is an above-threshold value (e.g., indicating that an individual is likely to have a rare disease and/or should be referred for a rare disease screening/investigation) and the outcome of a subsequent rare disease screening/investigation is positive (i.e., the individual is diagnosed by a clinician as having a rare disease), then the recommendation validation indicator may be positive. Similarly, if the predicted risk score/initial risk score is a below-threshold value (e.g., indicating that the individual is not likely to have a rare disease and should not be referred for a rare disease screening/investigation) and the outcome of a subsequent rare disease screening/investigation is negative (i.e., the individual is not diagnosed by a clinician as having a rare disease), then the recommendation validation indicator may also be positive. Conversely, if the predicted risk score/initial risk score is a below-threshold value (e.g., indicating that the individual is not likely to have a rare disease and should not be referred for a rare disease screening/investigation) and the outcome of a subsequent rare disease screening/investigation is positive (i.e., the individual is diagnosed by a clinician as having a rare disease), then the recommendation validation indicator may be negative.

The term "patient profile" may refer to a data object storing and/or providing access to information/data associated with a patient/individual. The patient profile may also comprise member information/data, member features, and/or similar words used herein interchangeably that can be associated with a given member identifier for a patient/individual, claim, and/or the like. In some embodiments, member information/data can include age, gender, known health conditions, home location, medical history, claim history, member identifier (ID), and/or the like.

The term "sensor data" may refer to user information/data, physiological information/data, biometric information/ data, location information/data, environmental information/data, image/video sensor information/data, and/or the like which may be associated with a particular individual. Sensor data may be collected and/or generated by one or more sensors associated with the user, such as mobile device sensors, wearable device sensors, sensors associated with one or more devices commonly used by the user, and/or the like. In some embodiments, the sensor data may include image data, muscle condition data, heart rate data, oxygen saturation data, pulse rate data, body temperature data, breath rate data, perspiration data, blink rate data, blood pressure data, neural activity data, cardiovascular data, pulmonary data, and/or various other types of information/data. In some embodiments, sensor data may be stored in conjunction with a user profile and/or input feature data object.

The term "electronically coupled" or "in electronic communication with" may refer to two or more electrical elements (for example, but not limited to, an example processing circuitry, communication module, input/output module memory, plurality of independent foot stimulation sections) and/or electric circuit(s) being connected through wired means (for example but not limited to, conductive wires or traces) and/or wireless means (for example but not limited to, wireless network, electromagnetic field), such that data and/or information (for example, electronic indications, signals) may be transmitted to and/or received from the electrical elements and/or electric circuit(s) that are electronically coupled.

III. Computer Program Products, Methods, and Computing Devices

Embodiments of the present disclosure may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In some embodiments, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In some embodiments, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of a data structure, apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 provides an example system architecture 100 that can be used in conjunction with various embodiments of the present disclosure. As shown in FIG. 1, the system architecture 100 may comprise one or more risk prediction computing entities 10, one or more user computing entities 20, one or more networks 30, one or more wearable devices 40 and/or the like. The example system architecture 100 may facilitate predicted risk scores that can be used to perform one or more prediction-based tasks. Each of the components of the system may be in electronic communication with, for example, one another over the same or different wireless or wired networks 30 including, for example, a wired or wireless Personal Area Network (PAN), Local Area Network (LAN), Metropolitan Area Network (MAN), Wide Area Network (WAN), and/or the like, as well as any hardware, software and/or firmware required to implement it (such as, e.g., network routers, and/or the like). Additionally, while FIG. 1 illustrates certain system devices as separate, standalone devices, the various embodiments are not limited to this architecture.

In some embodiments, the one or more risk prediction computing entities 10 are configured to receive data from one or more user computing entities 20/wearable devices (e.g., client computing entities) and process the data to generate predictive outputs (e.g., predicted risk scores) and provide the outputs to the client computing entities (e.g., for generating user interface data and/or dynamically updating a user interface). The one or more risk prediction computing entities 10 may be configured to receive queries, requests and/or data from client computing entities, process the queries, requests and/or data to generate predictive outputs, and provide (e.g., transmit, send, and/or the like) the predictive outputs to the client computing entities. The one or more risk prediction computing entities 10 may include a storage subsystem that is configured to store at least a portion of the data (e.g., operational instructions and parameters) utilized by the one or more risk prediction computing entity 10 to perform risk prediction operations and tasks. The risk prediction computing entity 10 may include one or more storage units, such as multiple distributed storage units that are connected through a computer network. Each storage unit in the storage subsystem may store at least one of one or more data assets and/or one or more data about the computed properties of one or more data assets. Moreover, each storage unit in the storage subsystem may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As further depicted in FIG. 1, the example system architecture 100 may include a wearable device 40. In various embodiments, the wearable device 40 is configured to obtain sensor data, such as image/video sensor data that can be used to determine one or more three-dimensional body-related characteristics and/or a three dimensional movement profile for a user. The wearable device 40 may be or comprise an article configured to be worn proximate or adjacent a portion of the wearer's body. In some embodiments, the wearable device 40 may be or comprise a jacket, vest, shirt, pants, shorts, underwear, hat, socks, scarf, neck warmer, leg gaiter, head band, arm band, leg band, and/or the like.

Exemplary Risk Prediction Computing Entity

FIG. 2 provides a schematic of a risk prediction computing entity 10 according to some embodiments of the present disclosure. In general, the terms computing device, entity, device, system, and/or similar words used herein interchangeably may refer to, for example, one or more computers, computing devices, computing entities, desktop computers, mobile phones, tablets, phablets, notebooks, laptops, distributed systems, terminals, servers or server networks, blades, gateways, switches, processing devices, set-top boxes, relays, routers, network access points, base stations, the like, and/or any combination of devices adapted to perform the functions, operations, and/or processes described herein. Such functions, operations, and/or processes may include, for example, transmitting, receiving, operating on, processing, displaying, storing, determining, generating/creating, monitoring, evaluating, comparing, and/or similar terms used herein interchangeably. In some embodiments, these functions, operations, and/or processes can be performed on data, content, information, and/or similar terms used herein interchangeably.

As indicated, in some embodiments, the risk prediction computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like.

As shown in FIG. 2, In some embodiments, the risk prediction computing entity 10 may include or be in communication with one or more processing elements 205 (also referred to as processors, processing circuitry, and/or similar terms used herein interchangeably) that communicate with other elements within the risk prediction computing entity 10 via a bus, for example. As will be understood, the processing element 205 may be embodied in a number of different ways. For example, the processing element 205 may be embodied as one or more complex programmable logic devices (CPLDs), microprocessors, multi-core processors, coprocessing devices, application-specific instruction-set processors (ASIPs), and/or controllers. Further, the processing element 205 may be embodied as one or more other processing devices or circuitry. The term circuitry may refer to an entire hardware embodiment or a combination of hardware and computer program products. Thus, the processing element 205 may be embodied as integrated circuits, application specific integrated circuits (ASICs), field-programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In some embodiments, the risk prediction computing entity 10 may further include or be in communication with non-volatile media (also referred to as non-volatile storage, memory, memory storage, memory circuitry and/or similar terms used herein interchangeably). In some embodiments, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

In some embodiments, the risk prediction computing entity 10 may further include or be in communication with volatile media (also referred to as volatile storage, memory, memory storage, memory circuitry and/or similar terms used herein interchangeably). In some embodiments, the volatile storage or memory may also include one or more volatile storage or memory media 215 as described above, such as RAM, DRAM, SRAM, FPM DRAM, EDO DRAM, SDRAM, DDR SDRAM, DDR2 SDRAM, DDR3 SDRAM, RDRAM, RIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the risk prediction computing entity 10 with the assistance of the processing element 205 and the operating system.

As indicated, in some embodiments, the risk prediction computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, risk prediction computing entity 10 may be configured to communicate via wireless external communication networks using any of a variety of protocols, such as general packet radio service (GPRS), Universal Mobile Telecommunications System (UMTS), Code Division Multiple Access 200 (CDMA200), CDMA200 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), IR protocols, NFC protocols, RFID protocols, IR protocols, ZigBee protocols, Z-Wave protocols, 6LoWPAN protocols, Wibree, Bluetooth protocols, wireless universal serial bus (USB) protocols, and/or any other wireless protocol. The risk prediction computing entity 10 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the risk prediction computing entity's components may be located remotely, such as in a distributed system. Furthermore, one or more of the components may be aggregated and additional components performing functions described herein may be included in the risk prediction computing entity 10. Thus, the risk prediction computing entity 10 can be adapted to accommodate a variety of needs and circumstances, such as including various components described with regard to a mobile application executing on the user computing entity 20, including various input/output interfaces.

Exemplary User Computing Entity

The exemplary user computing entity 20 may be in communication with the risk prediction computing entity 10 and the wearable device 40. The user computing entity 20 may obtain and provide (e.g., transmit/send) data objects describing raw data (e.g., sensor data and/or physiological data associated with the user) obtained by one or more additional sensors or sensing devices, captured by another user computing entity 20 or device and/or provided by another computing entity. The user computing entity 20 may be configured to provide (e.g., transmit, send) data objects describing at least a portion of the sensor data and/or physiological data to the risk prediction computing entity 10. Additionally, in various embodiments, a remote computing entity may provide data objects describing user information/data to the risk prediction computing entity 10. In some embodiments, a user (e.g., wearer) of the wearable device 40 may operate the wearable device 40 via the display 316 or keypad 318 of the user computing entity 20. In some embodiments, another person may operate the wearable device 40 on behalf of the individual (e.g., child).

FIG. 3 provides an illustrative schematic representative of user computing entity 20 that can be used in conjunction with embodiments of the present disclosure. In various embodiments, the user computing entity 20 may be or comprise one or more mobile devices. For example, a user computing entity 20 may be embodied as a user's mobile device, carried by the user, or operated by another person on behalf of the user, and therefore the user computing entity 20 may be in close proximity to a wearable device 40 worn by the user, such that close-range wireless communication technologies may be utilized for communicating between a controller of a wearable device 40 and the user computing entity 20.

As shown in FIG. 3, a user computing entity 20 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various devices, such as a risk prediction computing entity 10, another user computing entity 20, and/or the like. In an example embodiment, the transmitter 304 and/or receiver 306 are configured to communicate via one or more SRC protocols. For example, the transmitter 304 and/or receiver 306 may be configured to transmit and/or receive information/data, transmissions, and/or the like of at least one of Bluetooth protocols, low energy Bluetooth protocols, NFC protocols, RFID protocols, IR protocols, Wi-Fi protocols, ZigBee protocols, Z-Wave protocols, 6LoWPAN protocols, and/or other short range communication protocol. In various embodiments, the antenna 312, transmitter 304, and receiver 306 may be configured to communicate via one or more long range protocols, such as GPRS, UMTS, CDMA200, 1×RTT, WCDMA, GSM, EDGE, TD-SCDMA, LTE, E-UTRAN, EVDO, HSPA, HSDPA, Wi-Fi, Wi-Fi Direct, WiMAX, and/or the like. The user computing entity 20 may also include one or more network and/or communications interfaces 320 for communicating with various computing entities, such as by communicating data, content, information, and/or similar terms used herein interchangeably that can be transmitted, received, operated on, processed, displayed, stored, and/or the like.

In this regard, the user computing entity 20 may be capable of operating with one or more air interface standards, communication protocols, modulation types, and access types. More particularly, the user computing entity 20 may operate in accordance with any number of wireless communication standards and protocols. In a particular embodiment, the user computing entity 20 may operate in accordance with multiple wireless communication standards and protocols, such as GPRS, UMTS, CDMA200, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 20 can communicate with various other devices using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 20 can also download changes, add-ons, and updates, for instance, to its firmware, software (e.g., including executable instructions, applications, program modules), and operating system.

According to some embodiments, the user computing entity 20 may include location determining aspects, devices, modules, functionalities, and/or similar words used herein interchangeably to acquire location information/data regularly, continuously, or in response to certain triggers. For example, the user computing entity 20 may include outdoor positioning aspects, such as a location module adapted to acquire, for example, latitude, longitude, altitude, geocode, course, direction, heading, speed, UTC, date, and/or various other information/data. In some embodiments, the location module can acquire information/data, sometimes known as ephemeris information/data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the apparatus's 30 position in connection with a variety of other systems, including cellular towers, Wi-Fi access points, and/or the like. Similarly, the user computing entity 20 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE transmitters, NFC transmitters, and/or the like. These indoor positioning aspects can be used in a variety of settings to determine the location of someone or something to within inches or centimeters.

The user computing entity 20 may also comprise a user interface device comprising one or more user input/output interfaces (e.g., a display 316 and/or speaker/speaker driver coupled to a processing element 308 and a touch interface, keyboard, mouse, and/or microphone coupled to a processing element 308). For example, the user interface may be configured to provide a mobile application, browser, interactive user interface, dashboard, webpage, and/or similar words used herein interchangeably executing on and/or accessible via the user computing entity 20 to cause the display or audible presentation of information/data and for user interaction therewith via one or more user input interfaces. Moreover, the user interface can comprise or be in communication with any of a number of devices allowing the user computing entity 20 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 20 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 20 can capture, collect, store information/data, user interaction/input, and/or the like.

The user computing entity 20 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, information/data, applications, programs, program modules, scripts, source code, object code, byte code, compiled code, interpreted code, machine code, executable instructions, and/or the like to implement the functions of the user computing entity 20.

V. Exemplary System Operations

As described below, the apparatuses, systems, and methods described herein provide techniques for improving operational reliability and computational efficiency of risk prediction predictive data analysis solutions by using a hierarchical risk prediction machine learning framework. As further described herein, a hierarchical risk prediction machine learning framework may selectively deploy a particular machine learning model/component while simultaneously performing training operations on another machine learning model/component. For example, a hierarchical risk prediction machine learning framework may generate predictive outputs using an initially-deployed risk prediction machine learning model and use the outputs of the initially-deployed risk prediction machine learning model to generate training data for a dynamically-deployed risk prediction machine learning model. In some embodiments, the outputs generated by the initially-deployed risk prediction machine learning model may be anonymized and deidentified to provide comprehensive training data that excludes personally identifiable information (PII). Additionally, using the noted hierarchical framework, deployment of the dynamically-deployed risk prediction machine learning model may be deferred until a target performance threshold is reached. Accordingly, by using a hierarchical risk prediction machine learning framework, various embodiments of the present invention optimize and improve the process of training dynamically-deployed risk prediction machine learning models while facilitating generation of useful predictive outputs during the training process. Thus, the solutions described herein improve operational reliability and computational efficiency of risk prediction data analysis solutions.

As further described below, various embodiments of the present invention disclose techniques for more efficiently and reliably performing predictive data analysis. For example, various embodiments of the present invention disclose techniques for performing predictive data analysis operations utilizing a hierarchical risk prediction machine learning framework. For example, according to some embodiments of the present invention, predictive data analysis using a hierarchical risk prediction machine learning framework can be performed by: (i) generating an initial risk score associated with an input feature data object using an initially-deployed risk prediction machine learning model of the hierarchical risk prediction machine learning framework, (ii) generating an adjusted risk score associated with an input feature data object using a dynamically-deployed risk prediction machine learning model of the hierarchical risk prediction machine learning framework, (iii) generating a predicted risk score using a risk aggregation machine learning model of the hierarchical risk prediction machine learning framework based at least in part on the initial risk score and the adjusted risk score, and (iv) performing one or more prediction-based actions based at least in part on the predicted risk score.

As further described below, various embodiments of the present invention describe techniques for increasing efficiency of machine learning frameworks while maintaining the outputs of the machine learning frameworks within a desired threshold accuracy/reliability range. For example, in some embodiments, a hierarchical machine learning framework includes an initially-deployed component and a dynamically-deployed component, where the initially-deployed component is trained using training data that is available before deployment of the hierarchical machine learning framework but is expected to be less accurate, while the dynamically-deployed component is trained using training data that is available after deployment of the hierarchical machine learning framework but is expected to be more accurate. This approach ensures that, before the training data for the dynamically-deployed component is available, the hierarchical machine learning framework only comprises the initially-deployed component and thus avoids the need for performing computational instructions associated with executing operations of the dynamically-deployed component of the hierarchical machine learning framework. In this way, by disclosing a hierarchical machine learning framework includes an initially-deployed component and a dynamically-deployed component, various embodiments of the present invention introduce techniques for increasing efficiency of machine learning frameworks while maintaining the outputs of the machine learning frameworks within a desired threshold accuracy/reliability range.

As further described below, various embodiments of the present invention improve data security of implementing machine learning frameworks using a client-server architecture, where the input features of a machine learning framework are provided by a client device to a predictive data analysis server system. For example, in some embodiments, at least part of the input data provided by the client device (e.g., image/video data associated with an identifiable feature data object) are removed after performing predictive inferences and thus not permanently maintained. In some embodiments, an input feature data object is associated with an identifiable feature data object that is removed from a storage subsystem associated with a predictive data analysis system after generating a predictive output (e.g., an initial risk and/or a predicted risk score) based at least in part on the input feature data object. In some embodiments, an input feature data object is associated with a deidentified three-dimensional model that is permanently stored and/or not removed from a storage subsystem associated with a predictive data analysis system after generating a predictive output (e.g., an initial risk and/or a predicted risk score) based at least in part on the input feature data object. In some embodiments, the deidentified three-dimensional model is used as input data for a dynamically-deployed component of a machine learning framework, while the identifiable feature data object is used as input data for an initially-deployed component of the machine learning framework. In this way, if the predictive data analysis system is compromised, only permanently-stored data (e.g., de-identified data) are comprised, while identifiable data are not compromised. In this way, by ensuring that at least part of the input data provided by the client device (e.g., image/video data associated with an identifiable feature data object) are removed after performing predictive inferences and thus not permanently maintained, various embodiments of the present invention improve data security of implementing machine learning frameworks using a client-server architecture, where the input features of a machine learning framework are provided by a client device to a predictive data analysis server system.

Although the following exemplary operations are described as being performed by one of the risk prediction computing entity 10, user computing entity 20, or wearable device 40, it should be understood that in various embodiments, the operations can be interchangeably performed by other components within the system architecture 100.

Exemplary Techniques for Generating a Predicted Risk Score

In various embodiments, an example risk prediction computing entity 10 may be configured to generate a predicted risk score. The term predicted risk score may refer to a data object that describes an inferred measure of risk with respect to an input feature data object. For example, the predicted risk score may be related to whether a predictive entity (e.g., individual) that is associated with the input feature data object is likely to have a rare disease and/or should be referred for a rare disease screening/investigation (e.g., DNA sequencing/testing, clinician review, and/or the like). The example predicted risk score may be used to perform one or more prediction-based actions with respect to the input feature data object.

Referring now to FIG. 4, a flowchart diagram illustrating an example process 400 for generating a predicted risk score by a risk prediction computing entity 10 that leads to performing one or more prediction-based actions in accordance with some embodiments of the present disclosure is provided.

Beginning at step/operation 401, risk prediction computing entity 10 receives a risk scoring request for a predictive entity. In some embodiments, a predictive entity may describe an individual (e.g., child, patient, member, or the like). In some embodiments, a risk scoring request may be initiated by a parent that is concerned about a lack of a diagnosis or suspects that their child may have a rare disease. The risk scoring request may be generated by a computing entity (e.g., such as but not limited to, user computing entity 20) discussed above in connection with FIG. 1) operated by a user (e.g., parent or guardian). By way of example, where the predictive entity describes a child, a parent or guardian may enter information/data regarding the child via a user interface of a user computing entity. Such data may include details such as age, gender, number of siblings, known medical conditions/history for the child and/or family members, and/or the like. In various embodiments, a variety of sources (e.g., risk prediction computing entity 10) may provide (e.g., transmit, send) a mobile application for download and execution on a user computing entity 20 (e.g., in response to a request to download the mobile application generated at the user computing entity 20). In another embodiment, the mobile application may be pre-installed on the user computing entity 20. And in yet another embodiment, the mobile application may be a browser executing on the user computing entity 20. The mobile application may comprise computer-executable program code (e.g., a software application) that provides the functionality described herein. The mobile application may enable various functionalities as discussed herein. Moreover, although specifically referenced as a mobile application, it should be understood that the mobile application may be executable by any of a variety of computing entity types, such as desktop computers, laptop computers, mobile devices, and/or the like. In various embodiments, instructions may be automatically generated (e.g., by the risk prediction computing entity 10) or provided based at least in part in response to clinician input/instructions provided by a clinician interacting with the risk prediction computing entity 10. The instructions may comprise messages in the form of banners, headers, notifications, and/or the like. In some embodiments, step/operation 401 may include prompting a user (e.g., parent or guardian) to register or select a new case. The user may be guided through data protection and consent screens. In some examples, regulatory and compliance information may be provided detailing how the app may utilize uploaded data, and how long it may be retained. In some examples, a consent screen may relate to retention of deidentified three-dimensional models derived from image/video sensor data, as further discussed below. If a user provides consent, at least a portion of the data may be stored in a secure manner (e.g., in a risk prediction repository).

Returning to FIG. 4, subsequent to step/operation 401, the process 400 proceeds to step/operation 402. At step/operation 402, risk prediction computing entity 10 determines whether the predictive entity is associated with an input feature data object. An input feature data object may be or comprise a data object that describes features associated with a predictive entity (e.g., individual, child, patient, member, or the like). Accordingly, in some embodiments, step/operation 402 includes identifying an existing user profile stored in a user profile database. In such a case, risk prediction computing entity 10 may link the user to an existing input feature data object/user profile storing user data for a particular individual. Each input feature data object/user profile may be identifiable via one or more identifiers (e.g., social security numbers, patient IDs, member IDs, participant IDs, usernames, one or more globally unique identifiers (GUIDs), universally unique identifiers (UUIDs), and/or the like) that are configured to uniquely identify the user.

Subsequent to step/operation 402, in an instance in which risk prediction computing entity 10 determines that the predictive entity is not associated with an input feature data object, the process 400 proceeds to step/operation 403. At step/operation 403, risk prediction computing entity 10 generates the input feature data object based at least in part on user-entered data. In some embodiments, generating the input feature data object may be performed as part of registering a user. In some embodiments, as part of registering a user, risk prediction computing entity 10 may obtain (e.g., request and receive) various data objects describing information/data associated with a user.

Referring now to FIG. 7, an example view of a user interface 700, in accordance with certain embodiments of the present disclosure is provided. In some embodiments, and as depicted in FIG. 7, a user may be guided through a series of questions relating to a child for whom the concern is raised. These questions may include known pre-existing medical conditions, age, gender, ethnicity. Additionally, as shown, a free-text input box may also be provided for additional information that may be relevant, thus enabling a parent or guardian to "raise their hand" about their concerns. In various embodiments, the user-entered data may be used as in input to one or more machine learning models. As illustrated, the core data capture via the user interface may be minimal. In some embodiments, the user interface protocol may include a simple consent tool, informing a parent or guardian that the data provided may be transmitted to a secure server and subsequently deleted unless further action is required, in which case the parent or guardian may be prompted for permission to transfer the data to a clinical expert. In some embodiments, if consent is given for more detailed data capture, then the user interface protocol may include asking the parent/guardian more detailed questions. In some examples, detailed questions may be designed to capture basic elements of a specialist pediatrician's review of systems, providing more robust and actionable data for the particular case under consideration.

Returning to FIG. 4, the process 400 proceeds to step/operation 404 and risk prediction computing entity 10 retrieves the input feature data object. In various embodiments, the input feature data object may describe various types of information associated with a particular user including, but not limited to, age, gender, weight/weight distribution, height, body mass index (BMI), and/or the like. In some embodiments, user profile data objects describing user information may be provided by one or more computing entities, one or more other wearable devices 40 (e.g., health management devices, fitness trackers, and/or the like), a mobile device and/or the like. In some embodiments, risk prediction computing entity 10 retrieves one or more data objects (e.g., via various API calls) describing the user information/data for generation/creation of and/or storage in conjunction with an input feature data object. In some embodiments, a user's electronic medical record (EMR) and/or third-party data/information (e.g., Face2Gene data) may be associated with and/or otherwise stored in conjunction with the input feature data object. In some examples, risk prediction computing entity 10 processes at least a portion of the received information (e.g., user-entered data, third-party data/information, EHR data) in order to extract human phenotype ontology (HPO) data from structured/unstructured data. In some embodiments, a user may be prompted to connect to a corresponding medical record source (e.g., Nutanix Cluster Check (NCC) or PicnicHealth account).

In various examples, risk prediction computing entity 10 may generate user interface data in order to facilitate capture of image/video sensor data, physiological data (e.g., via a wearable device 40), combinations thereof, and/or the like associated with the predictive entity (e.g., individual or child) by a user (e.g., parent or guardian). In some embodiments, the user interface data may be based at least in part on a clinical protocol developed with the input of pediatricians, rare disease experts/clinicians, neurologists and machine learning experts specializing in computer vision. The example clinical protocol may be associated with features, traits, and clinical signs that a rare disease expert would evaluate in an in-person consultation with a patient. The clinical protocol may comprise holistic characteristics, head and face characteristics, arm length characteristics, posture and muscle tone characteristics, and hand, finger and toe-related characteristics. Table 1 below provides an exemplary list of features, traits and clinical signs that may be used to develop a protocol/generate user interface data for capturing image/video sensor data.

TABLE 1

Acquisition of clinically-observable features and characteristics from image and video sensor data

| Feature, Trait or Clinical Sign | Data Acquired by Image, Video or Both |
|---|---|
| **Holistic Characteristics** | |
| Overall gestalt of the patient: do they look ill? | Both |
| Do they appear comfortable or are they struggling to breathe? | Video |
| Do they look well-nourished? | Both |
| Is the body itself proportionate, or are the limbs shorter than they should be? (clinical heuristics for arm span from "Handbook of Physical Measurements" for example). | Image |
| Are there skin markings-spots that are typical or atypical? | Image |
| Is the child's behavior appropriate for their age? E.g., a ten year old having tantrums? | Video |
| Is an infant crying inconsolably? | Video |
| **Head and Face** | |
| Does the head look particularly small or large? | Image |
| What is the hair patten? | Image |
| Eyebrows normally placed? | Image |
| What is the complexion-sallow, pale, robust, perfused? | Image |
| Familial facial resemblance, or disparate from the family? Typical appearance to an individual? | Image |
| Ears normally placed and shaped? | Image |
| Eyes too far apart or too close together-normally placed and shaped? | |
| Is there any suggestion in the face of any kind of clefting? E.g., subtle linear marks over the lips? | Image |
| Is the child swallowing and breathing OK? | Video |
| Is the child drooling? | Video |
| **Arm Length** | |
| Infants: hands should be able to reach the genitalia. | Image |
| Tips of fingers should hit about a ⅓ of the way down between hip/knee | Image |
| **Posture and Muscle Tone** | |
| Child with low tone will slump and slide through - part of the protocol could be to ask the parent to hold the child up. | Video |
| Is the child standing, sitting, or being held by the parent? | Video |
| Is their muscle tone appropriate? Are they being melded into the parents' arms? | |
| **Hands, Fingers and Toes** | |
| Any restrictions in the way the hands are open or extend? Do they hyperextend? Any joints restricted? | Video |
| Fingers and toes: normally shaped? | Both |
| Nails normal, do they ridge in an unusual way? | Image |

In some embodiments, a user may be prompted/directed to capture images of particular areas of the body (e.g., the face, the head, the torso, and/or the like) in various positions (e.g., supine, standing, and the like) via an image sensor (e.g., camera) of a user computing entity (e.g., mobile device). Additionally, a user may be prompted/directed to obtain image data via an image sensor/camera of the user computing entity for performing gait analysis by the risk prediction computing entity 10. In some embodiments, at least a portion of the sensor data (image/video sensor data and/or other sensor data) obtained via the user computing entity 20 and/or wearable device 40 may be transferred to the risk prediction computing entity 10 for performing at least a portion of the required operations. The wearable device 40 or user computing entity 20 may be configured to provide information/data in response to requests/queries received from the risk prediction computing entity 10. In various embodiments, the data may be transferred to the risk prediction computing entity 10 which may provide a pseudo-ID to associate particular image/video sensor data therewith.

Referring now to FIG. 8, an operational example 800 in accordance with some embodiments of the present disclosure is provided. In particular, FIG. 8 depicts image/video sensor data of a candidate individual that can be processed by the risk prediction computing entity 10. The risk prediction computing entity 10 processes the image/video sensor data in order to identify particular features/characteristics of the individual. As shown, risk prediction computing entity 10 processes the image/video sensor data to identify bilateral arm flexion and balanced gait which may be indicative of a typical movement profile. In some embodiments, risk prediction computing entity 10 may process image/video sensor data to determine a walking speed for the individual.

Returning to FIG. 4, subsequent to generating the input feature data object at step/operation 403 or retrieving the input feature data object at step/operation 404, the process 400 proceeds to step/operation 405. At step/operation 405, risk prediction computing entity 10 performs validation on image/video sensor data associated with the input feature data object. In some embodiments, performing validation on image/video sensor data may include evaluating the image/video sensor data to verify that it is of sufficient qualitative and quantitative quality (e.g., minimum size, duration, number of frames, and/or the like) for subsequent operations of the risk prediction computing entity 10. In some embodiments, risk prediction computing entity 10 performs an automated quality control pre-processing step, in order to ensure that the data is suitable for subsequent processing (e.g., sufficient brightness, clarity, minimal amount of blurring, sufficient image sharpness, resolution, and/or the like). In some examples, risk prediction computing entity 10 may proceed to pre-process at least a portion of the captured data and/or transmit requests for additional images and/or video if the data provided is of insufficient qualitative and/or quantitative quality. In some embodiments, pre-processing steps/operations may include determining various measurements/parameters from the image/video sensor data (e.g., head circumference, arm length, gaze estimation, gesture recognition, and/or the like) that can be used to generate quantitative comparisons.

Referring now to FIG. 9A and FIG. 9B, example views of user interfaces 900A and 900B, in accordance with certain embodiments of the present disclosure are provided. As depicted in FIG. 9A, a user may be prompted to take a photo of a subject's head from a plurality of positions (e.g., sagittal and/or transverse image captures). Additionally, a user may be prompted to capture one or more videos (e.g., of a subject/child walking) that can be used for gait analysis. The image/video sensor data may be transmitted to risk prediction computing entity 10 for use as inputs to one or more trained deep learning/computer vision-based machine learning models that has been trained to detect subtle nuances potentially representative as indicative signs of an underlying rare disease. As further depicted in FIG. 9B, in response to determining that the provided image/video sensor data fails to satisfy certain predetermined quality thresholds, the user may be prompted to provide new data (e.g., as shown, retake a photo). In some embodiments, templates for acceptable images and videos may be provided via the user interface to guide users.

Returning to FIG. 4, subsequent to performing validation on image/video sensor data at step/operation 405, the process 400 proceeds to step/operation 406. At step/operation 406, risk prediction computing entity 10 generates a predicted risk score for the input feature data object. In some embodiments, the predicted risk score may be a value where an above-threshold value indicates that a particular individual is likely to have a rare disease and/or should be referred for a rare disease screening/investigation. In some embodiments, risk prediction computing entity 10 uses deep learning machine learning models and computer vision/image segmentation processing techniques (e.g., via a SoftMax layer) to generate the predicted risk score.

Subsequent to step/operation 406, the process 400 proceeds to step/operation 407. At step/operation 407, risk prediction computing entity 10 performs one or more prediction-based actions. In some embodiments, prediction-based tasks may include various intervention operations including generating a report and/or alerts for a user, automatically initiating a rare disease investigation (e.g., providing recommendations, scheduling an in-person visit, genomic testing, providing advocacy/support information/contacts, initiating enrollment in clinical trials, and/or the like). In some embodiments, exemplary recommendations may include: (i) recommending a review of the individual's health with a general practitioner, (ii) recommending engagement of a genetic counsellor for whole genome sequencing, and (iii) recommending a nearby rare disease specialist and/or Centre of Excellence for a face-to-face consultation. In some embodiments, if a consultation with a specialist is recommended, derived HPO terms and the associated image/video sensor data may be forwarded to a physician if appropriate and possible in advance of the consultation. In some embodiments, risk prediction computing entity 10 may retain at least a portion of the data associated with the individual in order to subsequently confirm whether the recommended outcome is successful and, in some examples, update corresponding weights/parameters of at least one component of a hierarchical risk prediction machine learning model framework accordingly. In some embodiments, risk prediction computing entity 10 may facilitate transfer of at least a portion of the data obtained with respect to an individual to a physician, consultant, or specialist in advance of a consultation.

Referring now to FIG. 5A, an operational example 406A for generating a predicted risk score in accordance with some embodiments of the present disclosure is provided.

As depicted in FIG. 5A, in various embodiments, risk prediction computing entity 10 uses an initially-deployed risk prediction machine learning model 502 to generate a predicted risk score 530. As illustrated, the initially-deployed risk prediction machine learning model is configured to process an input feature data object 503 (e.g., comprising image/video sensor data, other sensor data) in order to generate an identifiable feature data object 501. The identifiable feature data object 501 may be a data object describing identifiable features associated with a predictive entity, including a three-dimensional movement profile, one or more one or more three-dimensional body-related characteristics, patient information/data (e.g., historical claim data), contextual features (e.g., social media data) associated with an individual/related entities, an operational context of a machine learning model, and/or the like. The initially-deployed risk determination machine learning model may be utilized by the risk prediction computing entity 10 prior to deployment of a dynamically-deployed risk prediction machine learning model, as discussed in relation to FIG. 6 below. In particular, as depicted in FIG. 5A, the initially-deployed risk prediction machine learning model 502 processes the identifiable feature data object 501 in order to generate the predicted risk score 530.

Referring now to FIG. 5B, another operational example 406B for a predicted risk score in accordance with some embodiments of the present disclosure is provided. As depicted in FIG. 5B, in various embodiments, risk prediction computing entity 10 uses an initially-deployed risk prediction machine learning model 502 and a dynamically-deployed risk prediction machine learning model 504 to generate a predicted risk score 530. For example, the risk prediction computing entity 10 may trigger deployment of the dynamically-deployed risk prediction machine learning model in an instance in which one or more conditions are satisfied or met, as discussed in more detail below. As illustrated in FIG. 5B, risk prediction computing entity 10 processes an input feature data object 503 in order to generate an identifiable feature data object 501 and an input deidentified three-dimensional model 505. The input deidentified three-dimensional model 505 may be a data object that describes a deidentified three-dimensional movement profile and/or one or more three-dimensional body related characteristics associated with a predictive entity. An exemplary three-dimensional movement profile may comprise at least one movement feature set describing a three-dimensional representation of an individual's gait. Exemplary three-dimensional body-related characteristics may comprise at least one feature set describing a three-dimensional representation of an individual's physical characteristics (e.g., three-dimensional body-related characteristics may include holistic characteristics, head and face characteristics, posture, muscle tone, and arm and hand characteristics depicted in Table 1 above). As further depicted in FIG. 5B, in some embodiments, the initially-deployed risk prediction machine learning model 502 is configured to process the identifiable feature data object 501 in order to generate an initial risk score 507. In some embodiments, training examples for the initially-deployed risk prediction machine learning model 502 may include negative training examples (e.g., crowd-sourced videos of healthy children walking and children absent of the specific conditions under consideration and/or images of children with healthy head circumferences, acquired from multiple planes (e.g. transverse, sagittal, frontal, coronal) of appropriate quality for feature extraction (e.g., determined from the observables in Table 1). In some embodiments, the training examples for the initially-deployed risk prediction machine learning model may include positive training examples (e.g., acquired via clinical images used for physician training such as medical textbooks, determined implicitly by third-party (e.g., Face2Gene) training data, and/or pediatric neurology training videos.

As further depicted, the dynamically-deployed risk prediction machine learning model 504 is configured to process the input deidentified three-dimensional model 505 in order to generate an adjusted risk score 513. As illustrated, risk prediction computing entity 10 uses the initial risk score 507 and the adjusted risk score 513 as inputs to a risk aggregation machine learning model 520 for generating the predicted risk score 530. The risk aggregation machine learning model may be a supervised machine learning model or an unsupervised machine learning model (e.g., a clustering model). As illustrated in FIG. 5B, risk prediction computing entity 10 then uses the risk aggregation machine learning model 520 to generate the predicted risk score 530 based at least in part on the initial risk score 507 and the adjusted risk score 513.

Exemplary Techniques for Training Risk Prediction Machine Learning Models

Referring now to FIG. 6, a flowchart diagram illustrating an example process 600 for training and/or deploying a dynamically-deployed risk prediction machine learning model by a risk prediction computing entity 10 or another computing entity, in accordance with some embodiments of the present disclosure is provided.

Beginning at step/operation 602, the risk prediction computing entity 10 obtains (e.g., generates, receives, or the like) an identifiable feature data object. As noted above, the identifiable feature data object may describe identifiable features associated with an individual (e.g., a three-dimensional movement profile, one or more three-dimensional body-related characteristics, patient information/data, contextual features associated with an individual/related entities, and/or the like).

Subsequent to obtaining the identifiable feature data object at step/operation 602, the process 600 proceeds at step/operation 604. At step/operation 604, the risk prediction computing entity 10 generates an input deidentified three-dimensional model (e.g., describing a deidentified/anonymized three-dimensional representation of an individual's movement profile, gait, and/or body-related characteristics). The input deidentified three-dimensional model may describe the gross features associated with an individual—such as the dimensions of the head—but lack any identifiable information.

Subsequent to generating an input deidentified three-dimensional model at step/operation 604, the process 600 proceeds to step/operation 606. At step/operation 606, risk prediction computing entity 10 determines an initial risk score based at least in part on the input deidentified three-dimensional model and using an initially deployed risk prediction machine learning model.

Subsequent to determining the initial risk score at step/operation 606, the process 600 proceeds to step/operation 608. At step/operation 608, risk prediction computing entity 10 determines a recommendation validation indicator based at least in part on the initial risk score. The recommendation validation indicator may be a data object that describes a determination relating to a degree of correspondence between a risk score (e.g., initial risk score or predicted risk score) associated with a predicted recommendation and a validated outcome of a subsequent rare disease screening/investigation. For example, if a predicted risk score/initial risk score is an above-threshold value (e.g., indicating that an individual is likely to have a rare disease and/or should be referred for a rare disease screening/investigation) and the outcome of a subsequent rare disease screening/investigation is positive (i.e., the individual is diagnosed by a clinician as having a rare disease), then the recommendation validation indicator may be positive. Conversely, if the predicted risk score/initial risk score is a below-threshold value (e.g., indicating that the individual is not likely to have a rare disease and should not be referred for a rare disease screening/investigation) and the outcome of a subsequent rare disease screening/investigation is positive (i.e., the individual is diagnosed by a clinician as having a rare disease), then the recommendation validation indicator may be negative.

Subsequent to determining the recommendation validation indicator at step/operation 608, the process 600 proceeds to step/operation 610. At step/operation 610, risk prediction computing entity 10 generates a dynamic deployment training entry. In some embodiments, the dynamic deployment training entry may be a training entry deidentified three-dimensional model that is in turn associated with a corresponding training entry feature data object and a corresponding dynamic deployment ground-truth indicator. In some embodiments, the dynamic deployment ground-truth indicator may be a data object that describes a validated outcome of a rare disease screening or investigation. For example, a dynamic deployment ground-truth indicator may be associated with a training entry feature data object describing features of a deidentified individual that is identified as having a rare disease (e.g., as a result of a rare disease screening/investigation). In some embodiments, a training entry deidentified three-dimensional model may be a data object that describes a deidentified three-dimensional model/representation (e.g., comprising a deidentified three-dimensional movement profile and/or one or more three-dimensional body-related characteristics).

Subsequent to generating the dynamic deployment entry at step/operation 610, the process 600 proceeds to step/operation 612. At step/operation 612, risk prediction computing entity 10 trains a dynamically-deployed risk prediction machine learning model using the dynamic deployment training entry. In various embodiments, the risk prediction computing entity 10 may continue to generate initial risk scores using the initially-deployed risk prediction machine learning model and use the input deidentified three-dimensional model and associated recommendation validation indicators to generate training data (dynamic deployment training entries) for the dynamically-deployed risk prediction machine learning model.

As depicted in FIG. 6, at step/operation 614, risk prediction computing entity 10 determines whether a dynamic deployment training entry count satisfies a dynamic deployment training entry count threshold. The dynamic deployment training entry count threshold may refer a parameter, condition, value, or the like that defines count of dynamic deployment training entries that must be satisfied in order to trigger deployment of a dynamically-deployed risk determination machine learning model.

As further illustrated in FIG. 6, in an instance in which risk prediction computing entity 10 determines that the dynamic deployment training entry count fails to satisfy the dynamic deployment training entry count threshold, the process 600 returns to step/operation 602 where risk prediction computing entity 10 continues to process identifiable feature data objects.

At step/operation 614, in an instance in which risk prediction computing entity 10 determines that the dynamic deployment training entry count satisfies (e.g., exceeds) the dynamic deployment training entry count threshold, the process 600 proceeds to step/operation 616 and risk prediction computing entity 10 triggers deployments of the dynamically-deployed risk prediction machine learning model.

Accordingly, as described above, various embodiments of the present invention describe techniques for increasing efficiency of machine learning frameworks while maintaining the outputs of the machine learning frameworks within a desired threshold accuracy/reliability range. For example, in some embodiments, a hierarchical machine learning framework includes an initially-deployed component and a dynamically-deployed component, where the initially-deployed component is trained using training data that is available before deployment of the hierarchical machine learning framework but is expected to be less accurate, while the dynamically-deployed component is trained using training data that is available after deployment of the hierarchical machine learning framework but is expected to be more accurate. This approach ensures that, before the training data for the dynamically-deployed component is available, the hierarchical machine learning framework only comprises the initially-deployed component and thus avoids the need for performing computational instructions associated with executing operations of the dynamically-deployed component of the hierarchical machine learning framework. In this way, by disclosing a hierarchical machine learning framework includes an initially-deployed component and a dynamically-deployed component, various embodiments of the present invention introduce techniques for increasing efficiency of machine learning frameworks while maintaining the outputs of the machine learning frameworks within a desired threshold accuracy/reliability range.

As further described above, various embodiments of the present invention improve data security of implementing machine learning frameworks using a client-server architecture, where the input features of a machine learning framework are provided by a client device to a predictive data analysis server system. For example, in some embodiments, at least part of the input data provided by the client device (e.g., image/video data associated with an identifiable feature data object) are removed after performing predictive inferences and thus not permanently maintained. In some embodiments, an input feature data object is associated with an identifiable feature data object that is removed from a storage subsystem associated with a predictive data analysis system after generating a predictive output (e.g., an initial risk and/or a predicted risk score) based at least in part on the input feature data object. In some embodiments, an input feature data object is associated with a deidentified three-dimensional model that is permanently stored and/or not removed from a storage subsystem associated with a predictive data analysis system after generating a predictive output (e.g., an initial risk and/or a predicted risk score) based at least in part on the input feature data object. In some embodiments, the deidentified three-dimensional model is used as input data for a dynamically-deployed component of a machine learning framework, while the identifiable feature data object is used as input data for an initially-deployed component of the machine learning framework. In this way, if the predictive data analysis system is compromised, only permanently-stored data (e.g., de-identified data) are comprised, while identifiable data are not compromised. In this way, by ensuring that at least part of the input data provided by the client device (e.g., image/video data associated with an identifiable feature data object) are removed after performing predictive inferences and thus not permanently maintained, various embodiments of the present invention improve data security of implementing machine learning frameworks using a client-server architecture, where the input features of a machine learning framework are provided by a client device to a predictive data analysis server system.

VI. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only, and not for purposes of limitation.

The invention claimed is:

1. A computer-implemented method comprising:

generating, by one or more processors and based at least in part on an input feature data object, an input deidentified three-dimensional model;

generating, by the one or more processors, based at least in part on the input deidentified three-dimensional model, and using a dynamically-deployed risk prediction machine learning model, a predicted risk score for the input feature data object, wherein:

(i) the dynamically-deployed risk prediction machine learning model is deployed when a dynamic deployment training entry count of a plurality of dynamic deployment training entries satisfies a dynamic deployment training entry count threshold, (ii) the dynamically-deployed risk prediction machine learning model is trained using the plurality of dynamic deployment training entries, (iii) a dynamic deployment training entry of the plurality of dynamic deployment training entries comprises a corresponding training entry deidentified three-dimensional model that is associated with a corresponding training entry feature data object and a corresponding dynamic deployment ground-truth indicator, (iv) the corresponding dynamic deployment ground-truth indicator of a corresponding dynamic deployment training entry is determined based at least in part on a corresponding recommendation validation indicator for a corresponding predicted recommendation that is generated based at least in part on an initial risk score, and (v) the initial risk score is generated by an initially-deployed risk determination machine learning model based at least in part on an identifiable feature data object for the corresponding dynamic deployment training entry; and initiating, by the one or more processors, performance of a prediction-based action based at least in part on the predicted risk score.

2. The computer-implemented method of claim 1, wherein:

prior to deploying the dynamically-deployed risk prediction machine learning model, the predicted risk score for the input feature data object is generated based at least in part on a corresponding initial risk score generated by the initially-deployed risk determination machine learning model.

3. The computer-implemented method of claim 1, wherein the identifiable feature data object comprises image or video sensor data associated with the corresponding dynamic deployment training entry.

4. The computer-implemented method of claim 1, wherein the input deidentified three-dimensional model comprises a three-dimensional movement profile and a plurality of three-dimensional body-related characteristics.

5. The computer-implemented method of claim 4, wherein the plurality of three-dimensional body-related characteristics comprise a holistic characteristic, a head and face characteristic, a posture characteristic, a muscle tone characteristic, or an arm and hand characteristic.

6. The computer-implemented method of claim 1, wherein the dynamically-deployed risk prediction machine learning model is further configured to process a contextual feature associated with an operational context of the input deidentified three-dimensional model.

7. The computer-implemented method of claim 1, wherein the initially-deployed risk determination machine learning model comprises a convolutional neural network and an image-based classification machine learning component.

8. A system comprising:

one or more processors; and one or more memories storing processor-executable instructions that, when executed by the one or more processors, cause the one or more processors to perform operations comprising:

generating, based at least in part on an input feature data object, an input deidentified three-dimensional model;

generating, based at least in part on the input deidentified three-dimensional model, and using a dynamically-deployed risk prediction machine learning model, a predicted risk score for the input feature data object, wherein:

(i) the dynamically-deployed risk prediction machine learning model is deployed when a dynamic deployment training entry count of a plurality of dynamic deployment training entries satisfies a dynamic deployment training entry count threshold, (ii) the dynamically-deployed risk prediction machine learning model is trained using the plurality of dynamic deployment training entries, (iii) a dynamic deployment training entry of the plurality of dynamic deployment training entries comprises a corresponding training entry deidentified three-dimensional model that is associated with a corresponding training entry feature data object and a corresponding dynamic deployment ground-truth indicator, (iv) the corresponding dynamic deployment ground-truth indicator of a corresponding dynamic deployment training entry is determined based at least in part on a corresponding recommendation validation indicator for a corresponding predicted recommendation that is generated based at least in part on an initial risk score, and (v) the initial risk score is generated by an initially-deployed risk determination machine learning model based at least in part on an identifiable feature data object for the corresponding dynamic deployment training entry; and initiating performance of a prediction-based action based at least in part on the predicted risk score.

9. The system of claim 8, wherein:

prior to deploying the dynamically-deployed risk prediction machine learning model, the predicted risk score for the input feature data object is generated based at least in part on a corresponding initial risk score generated by the initially-deployed risk determination machine learning model.

10. The system of claim 8, wherein the identifiable feature data object comprises image or video sensor data associated with the corresponding dynamic deployment training entry.

11. The system of claim 8, wherein the input deidentified three-dimensional model comprises a three-dimensional movement profile and a plurality of three-dimensional body-related characteristics.

12. The system of claim 11, wherein the plurality of three-dimensional body-related characteristics comprise a holistic characteristic, a head and face characteristic, a posture characteristic, a muscle tone characteristic, or an arm and hand characteristic.

13. The system of claim 8, wherein the dynamically-deployed risk prediction machine learning model is further configured to process a contextual feature associated with an operational context of the input deidentified three-dimensional model.

14. The system of claim 8, wherein the initially-deployed risk determination machine learning model comprises a convolutional neural network and an image-based classification machine learning component.

15. One or more non-transitory computer-readable media storing processor-executable instructions that, when executed by one or more processors, cause the one or more processors to perform operations comprising:

generating, based at least in part on an input feature data object, an input deidentified three-dimensional model;

generating, based at least in part on the input deidentified three-dimensional model, and using a dynamically-deployed risk prediction machine learning model, a predicted risk score for the input feature data object, wherein:

(i) the dynamically-deployed risk prediction machine learning model is deployed when a dynamic deployment training entry count of a plurality of dynamic deployment training entries satisfies a dynamic deployment training entry count threshold, (ii) the dynamically-deployed risk prediction machine learning model is trained using the plurality of dynamic deployment training entries, (iii) a dynamic deployment training entry of the plurality of dynamic deployment training entries comprises a corresponding training entry deidentified three-dimensional model that is associated with a corresponding training entry feature data object and a corresponding dynamic deployment ground-truth indicator, (iv) the corresponding dynamic deployment ground-truth indicator of a corresponding dynamic deployment training entry is determined based at least in part on a corresponding recommendation validation indicator for a corresponding predicted recommendation that is generated based at least in part on an initial risk score, and (v) the initial risk score is generated by an initially-deployed risk determination machine learning model based at least in part on an identifiable feature data object for the corresponding dynamic deployment training entry; and initiating performance of a prediction-based action based at least in part on the predicted risk score.

16. The one or more non-transitory computer-readable media of claim 15, wherein prior to deploying the dynamically-deployed risk prediction machine learning model, the predicted risk score for the input feature data object is generated based at least in part on a corresponding initial risk score generated by the initially-deployed risk determination machine learning model.

17. The one or more non-transitory computer-readable media of claim 15, wherein the identifiable feature data object comprises image or video sensor data associated with the corresponding dynamic deployment training entry.

18. The one or more non-transitory computer-readable media of claim 15, wherein the input deidentified three-dimensional model comprises a three-dimensional movement profile and a plurality of three-dimensional body-related characteristics.

19. The one or more non-transitory computer-readable media of claim 18, wherein the plurality of three-dimensional body-related characteristics comprise a holistic characteristic, a head and face characteristic, a posture, a muscle tone characteristic, or an arm and hand characteristic.

20. The one or more non-transitory computer-readable media of claim 15, wherein the dynamically-deployed risk prediction machine learning model is further configured to process a contextual feature associated with an operational context of the input deidentified three-dimensional model.

* * * * *